United States Patent [19]
Lernmark et al.

[11] Patent Number: 6,025,176
[45] Date of Patent: *Feb. 15, 2000

[54] CLONING AND EXPRESSION OF HUMAN ISLET GLUTAMIC ACID DECARBOXYLASE AUTOANTIGEN

[75] Inventors: Ake Lernmark, Seattle, Wash.; Allan E. Karlsen, Valby, Denmark; Catherine E. Grubin, Seattle, Wash.; William Hagopian, Seattle, Wash.; Patrick J. O'Hara, Seattle, Wash.; Donald C. Foster, Seattle, Wash.

[73] Assignee: The Board of Regents of the University of Washington and ZymoGenetics, Inc., Seattle, Wash.

[*] Notice: This patent is subject to a terminal disclaimer.

[21] Appl. No.: 08/453,040

[22] Filed: May 30, 1995

Related U.S. Application Data

[62] Division of application No. 08/108,145, Aug. 17, 1993, Pat. No. 5,792,620, which is a continuation of application No. 07/883,492, May 15, 1992, abandoned, which is a continuation-in-part of application No. 07/702,162, May 15, 1991.

[51] Int. Cl.$^7$ .............................. C12N 9/14; C12P 21/06; A61K 38/00; A61K 38/04
[52] U.S. Cl. .......................... 435/195; 435/691; 530/324; 530/326; 530/329
[58] Field of Search ........................... 435/195, 7.4, 506, 435/69.1; 424/185.1; 530/325

[56] References Cited

U.S. PATENT DOCUMENTS

| | | |
|---|---|---|
| 4,952,507 | 8/1990 | Woodward . |
| 5,475,086 | 12/1995 | Tobin et al. .............................. 530/325 |
| 5,512,447 | 4/1996 | Baekkeskov et al. ..................... 435/7.4 |
| 5,674,978 | 10/1997 | Tobin et al. .............................. 530/326 |

FOREIGN PATENT DOCUMENTS

| | | |
|---|---|---|
| 383129 | 8/1990 | European Pat. Off. . |
| 90/07117 | 6/1990 | WIPO . |

OTHER PUBLICATIONS

Petersen et al., "Glutamic Acid Decarboxylase (GAD$_{65}$) Autoantibodies in Prediction of β–Cell Function and Remission in Recent–Onset IDDM After Cyclosporin Treatment," *Diabetes* 43:1291–1296, 1994.

Cram et al. Cloning and partial nucleotide sequence of human glutamic acid decarboxylase cDNA from brain and pancreatic islets. Biochemical and Biophysical Research Communications. vol. 176, No.3, pp. 1239–1244, May 15, 1991.

Okada et al. High concentration of GABA and high glutamate decarboxylase activity in rat pancreatic islets and human insulinoma. Science. vol. 194, issue 4265, pp. 620–622, Nov. 5, 1976.

Solimena et al. Autoantibodies to GABA–ergic neurons and pancreatic beta cells in stiff–man syndrome. New England Journal of Medicine. vol. 322, No. 22, pp. 1555–1560, May 31, 1990.

Wyborski et al. Characterization of a cDNA coding for rat glutamic acid decarboxylase. Molecular Brain Research. vol. 8, pp. 193–198, 1990.

Baekkeskov et al., "Autoantibodies in Newly Diagnosed Diabetic Children Immunoprecipitate Human Pancreatic Islet Cell Proteins" *Nature* 298:167–169 (Jul. 8, 1982).

(List continued on next page.)

*Primary Examiner*—Eggerton A. Campbell
*Assistant Examiner*—Devesh Srivastava
*Attorney, Agent, or Firm*—Townsend and Townsend and Crew

[57] ABSTRACT

Human pancreatic islet cell glutamic acid decarboxylase (GAD), an autoantigen involved in the development of insulin-dependent diabetes mellitus (IDDM), has been cloned, sequenced and expressed by recombinant means. Recombinant human islet cell GAD polypeptides and antibodies specific to the GAD polypeptides can be used in methods of diagnosis and treatment, including use in immunoadsorptive therapy and the induction of immune tolerance.

3 Claims, 7 Drawing Sheets

OTHER PUBLICATIONS

Baekkeskov et al., "Autoantibodies to a 64Kd Islet Cell Protein Precede the Onset of Spontaneous Diabetes in the BB Rat" *Science* 224:1348–1350 (Jun. 22, 1984).

Gerling et al., "Islet Cell and 64K Autoantibodies are Associated with Plasma IgG in Newly Diagnosed Insulin–dependent Diabetic Children" *J. Immunol.* 137:3782–3785 (Dec. 15, 1986).

Baekkeskov et al., "Antibodies to a 64,000 M, human islet Cell Antigen Precede the Clinical Onset of Insulin–dependent Diabetes" *J. Clin. Invest.* 79:926–937 (1987).

Kobayashi et al., "Glutamic Acid Decarboxylase cDNA: Nucleotide Sequence Encoding an Enzymatically Active Fusion Protein" *J. Neurosci.* 7:2768–2772 (Sep., 1987).

Atkinson et al., "Autoantibodies in Nonobese Diabetic Mice Immunoprecipitate 64,000–$M_r$ Islet Antigen" *Diabetes* 37:1587–1590 (Nov., 1988).

The Promega Catalogue (1988–89).

Baekkeskov et al., "Identification of the 64K Autoantigen in Insulin–Dependent Diabetes as the GABA–Synthesizing Enzyme Glutamic Acid Decarboxylase" *Nature* 347:151–156 (Sep. 13, 1990).

Persson et al., "Expression of the Neurotransmitter–Synthesizing Enzyme Glutamic Acid Decarboxylase in Male Germ Cells" *Mol. Cell. Biol.* 10:4701–4711 (Sep., 1990).

Julien et al., "Rat Brain Glutamic Acid Decarboxylase Sequence Deduced from a Cloned cDNA" *J. Neurochem.* 54: 703–705 (1990).

Katarova et al., "Molecular Identification of the 62kd Form of Glutamic Acid Decarboxylase from the Mouse" *Eur. J. Neuorsci.* 2:190–202 (1990).

Karlsen et al., "Cloning and Primary Structure of a Human Islet Isoform of Glutamic Acid Decarboxylase from Chromosome 10" *Proc. Natl. Acad. Sci. USA* 88:8337–8341 (Oct., 1991).

```
GGCACTCGCT GGCGACCTGC TCCAGTCTCC AAAGCCG ATG GCA TCT CCG GGC TCT
55                                          Met Ala Ser Pro Gly Ser
                                              1               5

GGC TTT TGG TCT TTC GGG TCG GAA GAT GGC TCT GGG GAT TCC GAG AAT
103
Gly Phe Trp Ser Phe Gly Ser Glu Asp Gly Ser Gly Asp Ser Glu Asn
             10              15              20

CCC GGC ACA GCG CGA GCC TGG TGC CAA GTG GCT CAG AAG TTC ACG GGC
    151
Pro Gly Thr Ala Arg Ala Trp Cys Gln Val Ala Gln Lys Phe Thr Gly
         25              30              35

GGC ATC GGA AAC AAA CTG TGC GCC CTG CTC TAC GGA GAC GCC GAG AAG
    199
Gly Ile Gly Asn Lys Leu Cys Ala Leu Leu Tyr Gly Asp Ala Glu Lys
         40              45              50

CCG GCG GAG AGC GGC GGG AGC CAA CCC CCG CGG GCC GCC GCC CGG AAG
    247
Pro Ala Glu Ser Gly Gly Ser Gln Pro Pro Arg Ala Ala Ala Arg Lys
 55              60              65              70

GCC GCC TGC GCC TGC GAC CAG AAG CCC TGC AGC TGC TCC AAA GTG GAT
    295
Ala Ala Cys Ala Cys Asp Gln Lys Pro Cys Ser Cys Ser Lys Val Asp
                 75              80              85

GTC AAC TAC GCG TTT CTC CAT GCA ACA GAC CTG CTG CCG GCG TGT GAT
    343
Val Asn Tyr Ala Phe Leu His Ala Thr Asp Leu Leu Pro Ala Cys Asp
             90              95             100

GGA GAA AGG CCC ACT TTG GCG TTT CTG CAA GAT GTT ATG AAC ATT TTA
    391
Gly Glu Arg Pro Thr Leu Ala Phe Leu Gln Asp Val Met Asn Ile Leu
            105             110             115

CTT CAG TAT GTG GTG AAA AGT TTC GAT AGA TCA ACC AAA GTG ATT GAT
    439
Leu Gln Tyr Val Val Lys Ser Phe Asp Arg Ser Thr Lys Val Ile Asp
            120             125             130

TTC CAT TAT CCT AAT GAG CTT CTC CAA GAA TAT AAT TGG GAA TTG GCA
    487
Phe His Tyr Pro Asn Glu Leu Leu Gln Glu Tyr Asn Trp Glu Leu Ala
135             140             145             150
```

*FIG. 2a*

```
GAC CAA CCA CAA AAT TTG GAG GAA ATT TTG ATG CAT TGC CAA ACA ACT
    535
Asp Gln Pro Gln Asn Leu Glu Glu Ile Leu Met His Cys Gln Thr Thr
              155             160             165

CTA AAA TAT GCA ATT AAA ACA GGG CAT CCT AGA TAC TTC AAT CAA CTT
    583
Leu Lys Tyr Ala Ile Lys Thr Gly His Pro Arg Tyr Phe Asn Gln Leu
              170             175             180

TCT ACT GGT TTG GAT ATG GTT GGA TTA GCA GCA GAC TGG CTG ACA TCA
    631
Ser Thr Gly Leu Asp Met Val Gly Leu Ala Ala Asp Trp Leu Thr Ser
        185             190             195

ACA GCA AAT ACT AAC ATG TTC ACC TAT GAA ATT GCT CCA GTA TTT GTG
    679
Thr Ala Asn Thr Asn Met Phe Thr Tyr Glu Ile Ala Pro Val Phe Val
        200             205             210

CTT TTG GAA TAT GTC ACA CTA AAG AAA ATG AGA GAA ATC ATT GGC TGG
    727
Leu Leu Glu Tyr Val Thr Leu Lys Lys Met Arg Glu Ile Ile Gly Trp
215             220             225             230

CCA GGG GGC TCT GGC GAT GGG ATA TTT TCT CCC GGT GGC GCC ATA TCT
    775
Pro Gly Gly Ser Gly Asp Gly Ile Phe Ser Pro Gly Gly Ala Ile Ser
              235             240             245

AAC ATG TAT GCC ATG ATG ATC GCA CGC TTT AAG ATG TTC CCA GAA GTC
    823
Asn Met Tyr Ala Met Met Ile Ala Arg Phe Lys Met Phe Pro Glu Val
              250             255             260

AAG GAG AAA GGA ATG GCT GCT CTT CCC AGG CTC ATT GCC TTC ACG TCT
    871
Lys Glu Lys Gly Met Ala Ala Leu Pro Arg Leu Ile Ala Phe Thr Ser
              265             270             275

GAA CAT AGT CAT TTT TCT CTC AAG AAG GGA GCT GCA GCC TTA GGG ATT
    919
Glu His Ser His Phe Ser Leu Lys Lys Gly Ala Ala Ala Leu Gly Ile
              280             285             290

GGA ACA GAC AGC GTG ATT CTG ATT AAA TGT GAT GAG AGA GGG AAA ATG
    967
Gly Thr Asp Ser Val Ile Leu Ile Lys Cys Asp Glu Arg Gly Lys Met
295             300             305             310
```

*FIG. 2b*

```
ATT CCA TCT GAT CTT GAA AGA AGG ATT CTT GAA GCC AAA CAG AAA GGG
    1015
Ile Pro Ser Asp Leu Glu Arg Arg Ile Leu Glu Ala Lys Gln Lys Gly
              315                 320                 325

TTT GTT CCT TTC CTC GTG AGT GCC ACA GCT GGA ACC ACC GTG TAC GGA
    1063
Phe Val Pro Phe Leu Val Ser Ala Thr Ala Gly Thr Thr Val Tyr Gly
              330                 335                 340

GCA TTT GAC CCC CTC TTA GCT GTC GCT GAC ATT TGC AAA AAG TAT AAG
    1111
Ala Phe Asp Pro Leu Leu Ala Val Ala Asp Ile Cys Lys Lys Tyr Lys
              345                 350                 355

ATC TGG ATG CAT GTG GAT GCA GCT TGG GGT GGG GGA TTA CTG ATG TCC
    1159
Ile Trp Met His Val Asp Ala Ala Trp Gly Gly Gly Leu Leu Met Ser
              360                 365                 370

CGA AAA CAC AAG TGG AAA CTG AGT GGC GTG GAG AGG GCC AAC TCT GTG
    1207
Arg Lys His Lys Trp Lys Leu Ser Gly Val Glu Arg Ala Asn Ser Val
375                 380                 385                 390

ACG TGG AAT CCA CAC AAG ATG ATG GGA GTC CCT TTG CAG TGC TCT GCT
    1255
Thr Trp Asn Pro His Lys Met Met Gly Val Pro Leu Gln Cys Ser Ala
              395                 400                 405

CTC CTG GTT AGA GAA GAG GGA TTG ATG CAG AAT TGC AAC CAA ATG CAT
    1303
Leu Leu Val Arg Glu Glu Gly Leu Met Gln Asn Cys Asn Gln Met His
              410                 415                 420

GCC TCC TAC CTC TTT CAG CAA GAT AAA CAT TAT GAC CTG TCC TAT GAC
    1351
Ala Ser Tyr Leu Phe Gln Gln Asp Lys His Tyr Asp Leu Ser Tyr Asp
              425                 430                 435

ACT GGA GAC AAG GCC TTA CAG TGC GGA CGC CAC GTT GAT GTT TTT AAA
    1399
Thr Gly Asp Lys Ala Leu Gln Cys Gly Arg His Val Asp Val Phe Lys
              440                 445                 450

CTA TGG CTG ATG TGG AGG GCA AAG GGG ACT ACC GGG TTT GAA GCG CAT
    1447
Leu Trp Leu Met Trp Arg Ala Lys Gly Thr Thr Gly Phe Glu Ala His
455                 460                 465                 470
```

*FIG. 2c*

```
GTT GAT AAA TGT TTG GAG TTG GCA GAG TAT TTA TAC AAC ATC ATA AAA
    1495
Val Asp Lys Cys Leu Glu Leu Ala Glu Tyr Leu Tyr Asn Ile Ile Lys
            475             480             485

AAC CGA GAA GGA TAT GAG ATG GTG TTT GAT GGG AAG CCT CAG CAC ACA
    1543
Asn Arg Glu Gly Tyr Glu Met Val Phe Asp Gly Lys Pro Gln His Thr
            490             495             500

AAT GTC TGC TTC TGG TAC ATT CCT CCA AGC TTG CGT ACT CTG GAA GAC
    1591
Asn Val Cys Phe Trp Tyr Ile Pro Pro Ser Leu Arg Thr Leu Glu Asp
            505             510             515

AAT GAA GAG AGA ATG AGT CGC CTC TCG AAG GTG GCT CCA GTG ATT AAA
    1639
Asn Glu Glu Arg Met Ser Arg Leu Ser Lys Val Ala Pro Val Ile Lys
    520             525             530

GCC AGA ATG ATG GAG TAT GGA ACC ACA ATG GTC AGC TAC CAA CCC TTG
    1687
Ala Arg Met Met Glu Tyr Gly Thr Thr Met Val Ser Tyr Gln Pro Leu
535             540             545             550

GGA GAC AAG GTC AAT TTC TTC CGC ATG GTC ATC TCA AAC CCA GCG GCA
    1735
Gly Asp Lys Val Asn Phe Phe Arg Met Val Ile Ser Asn Pro Ala Ala
            555             560             565

ACT CAC CAA GAC ATT GAC TTC CTG ATT GAA GAA ATA GAA CGC CTT GGA
    1783
Thr His Gln Asp Ile Asp Phe Leu Ile Glu Glu Ile Glu Arg Leu Gly
            570             575             580

CAA GAT TTA TAATAACCTT GCTCACCAAG CTGTTCCACT TCTCTAGAGA
    1832
Gln Asp Leu
        585
```

FIG. 2d

```
ACATGCCCTC AGCTAAGCCC CCTACTGAGA AACTTCCTTT GAGAATTGTG CGACTTCACA
    1892

AAATGCAAGG TGAACACCAC TTTGTCTCTG AGAACAGACG TTACCAATTA TGGAGTGTCA
    1952

CCAGCTGCCA AAATCGTAGG TGTTGGCTCT GCTGGTCACT GGAGTAGTTG CTACTCTTCA
    2012

GAATATGGAC AAAGAAGGCA CAGGTGTAAA TATAGTAGCA GGATGAGGAA CCTCAAACTG
    2072

GGTATCATTT GCACGTGCTC TTCTGTTCTC AAATGCTAAA TGCAAACACT GTGTATTTAT
    2132

TAGTTAGGTG TGCCAAACTA CCGTTCCCAA ATTGGTGTTT CTGAATGACA TCAACATTCC
    2192

CCCAACATTA CTCCATTACT AAAGACAGAA AAAATAAAA ACATAAAATA TACAAACATG
    2252

TGGCAACCTG TTCTTCCTAC CAAATATAAA CTTGTGTATG ATCCAAGTAT TTTATCTGTG
    2312

TTGTCTCTCT AAACCCAAAT AAATGTGTAA ATGTGGACAC AAAAAAAAAA AAAAAAA
    2370
```

FIG. 2e

CLONING AND EXPRESSION OF HUMAN ISLET GLUTAMIC ACID DECARBOXYLASE AUTOANTIGEN

RELATED CASES

This application is a divisional of Ser. No. 08/108,145, filed Aug. 17, 1993 (U.S. Pat. No. 5,792,620), which is a continuation of Ser. No. 07/883,492, filed May 15, 1992, (abandoned), which is continuation-in-part of application Ser. No. 07/702,162, filed May 15, 1991 (pending), of which are incorporated herein by reference.

GOVERNMENT SUPPORT

This invention was made with government support under grant numbers DK26190, DK33873, and DK41801 awarded by the National Institutes of Health/Juvenile Diabetes Foundation. The government has certain rights in the invention.

BACKGROUND OF THE INVENTION

γ-Aminobutyric acid (GABA) is a major inhibitory neurotransmitter of the mammalian central nervous system. The rate-limiting step in GABA biosynthesis is the decarboxylation of L-glutamic acid by glutamic acid decarboxylase (GAD). Little is known with certainty regarding the regulation of GAD activity or the expression of GAD genes. Despite its wide distribution in the brain, GAD protein is present in very small quantities and is very difficult to purify to homogeneity.

Studies of GAD have been hindered by the existence of multiple forms of the enzyme, which differ in molecular weight, kinetic properties, sequence (when known), and hydrophobic properties. For example, the presence of three different forms of GAD in porcine brain has been reported (Spink et al., *J. Neurochem.* 40:1113–1119 (1983)), as well as four forms in rat brain (Spink et al., *Brain Res.* 421:235–244 (1987)). A mouse brain GAD (Huang et al., *Proc. Natl. Acad. Sci. USA* 87:8491–8495 (1990)) and a GAD clone isolated from feline brain Kobayashi et al., *J. Neurosci.* 7:2768–2772 (1987)) have also been reported. At least two isomers of GAD have been reported in human brain. Chang and Gottlieb, *J. Neurosci.* 8:2123–2130 (1988).

Further complicating the characterization of distinct GAD isozymes is the fact that GADs are also found in tissues outside of the brain, which GADs have varying degrees of homology with brain GADS. For example, GADs are also expressed in germ cells of the testis, as has been reported for several different species, e.g., rat (Persson et al., in *Perspectives of Andrology*, M. Serio, (ed.), p. 129–138, Raven Press, NY (1989)), and in human, guinea pig, monkey, and mouse testis (Perrson et al., *Mol. Cell. Biol.* 10:4701–4711 (1990). The human testis GAD was shown to have a relatively high degree of overall nucleotide sequence homology to the feline brain GAD. The presence of GAD in the pancreas has also been described. Okada et al., *Science* 194:620–622 (1976), Garry et al, *J. Histochem. Cytochem.* 36:573–580 (1988), and Vincent et al., *Neuroendocrin.* 36:197–204 (1983).

A rare neurological disorder, termed Stiff-Man Syndrome (SMS), is associated with the presence of autoantibodies to GABA-secreting neurons. The predominant autoantigen for the autoantibodies in SMS has recently been shown to be a brain GAD. Solimena et al., *N. Engl. J. Med.* 318:1012–1020 (1988) and Solimena et al., N. *Engl. J. Med.* 322:1555–1560 (1990).

A small proportion of patients with insulin-dependent diabetes mellitus (IDDM) also develop SMS. It has been speculated that autoimmune mechanisms may precipitate the clinical onset of IDDM. The destruction of pancreatic β (beta)-cells in the islets of Langerhans typically precedes IDDM. This destruction is believed to be mediated by a massive infiltration by lymphocytes into the islets, and by the presence of circulating autoantibodies to the β-cells.

A major target of autoantibodies associated with the development of IDDM is a pancreatic β-cell antigen of relative molecular mass 64,000 (64K). Baekkeskov et al., *J. Clin. Invest.* 79:926–934 (1987). Antibodies to the 64K antigen are present in greater than about 80% of newly diagnosed patients and have been detected up to several years before clinical onset of IDDM, concomitant with a gradual loss of β-cells. The 64K antigen has recently been identified as GAD. Baekkeskov et al., *Nature* 347:151–156 (1990).

As with brain GADs, the purification of native human islet cell GAD has a number of disadvantages. Human islet GAD is only a trace protein and it would be impractical to isolate useful quantities from natural sources. For example, purification of native human islet cell GAD would require a large number of human pancreata, which itself poses a substantial obstacle. Further, purification from human tissues carries the risk of co-purifying infective agents such as the hepatitis viruses, retroviruses such as HIV-1 and HIV-2, and other viral agents. Not only does this present the possibility of infecting recipients of therapeutic products with such agents, but raises significant concerns among workers who manufacture and test these products as well as those who will use the products in diagnostic laboratories.

There is a need in the art, therefore, for safe methods of producing relatively large amounts of pure preparations of human islet cell GAD polypeptides. These polypeptides would be useful as, inter alia, therapeutic agents in the treatment of GAD-related diseases, such as IDDM, and in the diagnosis and monitoring of these diseases. Quite remarkably, the present invention fulfills these and other related needs through the use of recombinant DNA technology, thus eliminating the problem of viral contamination and providing commercially feasible quantities of human islet cell GAD polypeptides.

SUMMARY OF THE INVENTION

The present invention provides the ability to produce human islet cell GAD polypeptides by recombinant or synthetic means. The human islet GAD polypeptides so produced may or may not have the biological activity of the native enzyme, depending on the intended use. Accordingly, isolated and purified polynucleotides are described which code for the human islet GAD polypeptides, where the polynucleotides may be in the form of DNA, such as cDNA or genomic DNA, or RNA. Based on these sequences probes can be designed for hybridization to identify these and related genes or transcription products thereof which encode human islet cell GAD.

In related embodiments the invention concerns DNA constructs which comprise a transcriptional promoter, a DNA sequence which encodes the human islet cell GAD polypeptide, and optionally a transcriptional terminator, each operably linked for expression of the GAD polypeptide. The constructs are preferably used to transfect or transform host cells, preferably eukaryotic cells, more preferably mammalian or yeast cells. For large scale production the expressed human islet cell GAD polypeptides can be isolated from the cells by, for example, immunoaffinity purification. Small synthetic peptides can also be prepared which immunologically mimic GAD antigenic determinants or other regions of the GAD molecule.

The GAD polypeptides of the invention can also be used therapeutically, for example, to remove autoantibodies to the GAD islet cell autoantigens, conveniently by extracorporeal immunoadsorptive means. The GAD polypeptides described herein also can be formulated and administered as pharmaceutical compositions, especially when used to induce immunological tolerance in individuals predisposed to developing or already afflicted by disease caused by or related to autoantibodies to GAD autoantigens, such as in IDDM.

In other embodiments the GAD polypeptides find use as diagnostic reagents, detecting and/or quantitating the level of GAD autoantibodies in an individual of interest. These diagnostic methods and compositions can be used in conjunction with therapeutic approaches to GAD-related diseases, particularly the treatment of IDDM.

BRIEF DESCRIPTION OF THE DRAWINGS

FIGS. 2a–2e shows the nucleotide sequence and predicted primary structure of human islet GAD, where nucleotides and amino acids are numbered at the left ends of the lines.

DESCRIPTION OF THE SELECTED EMBODIMENTS

Figure 1:
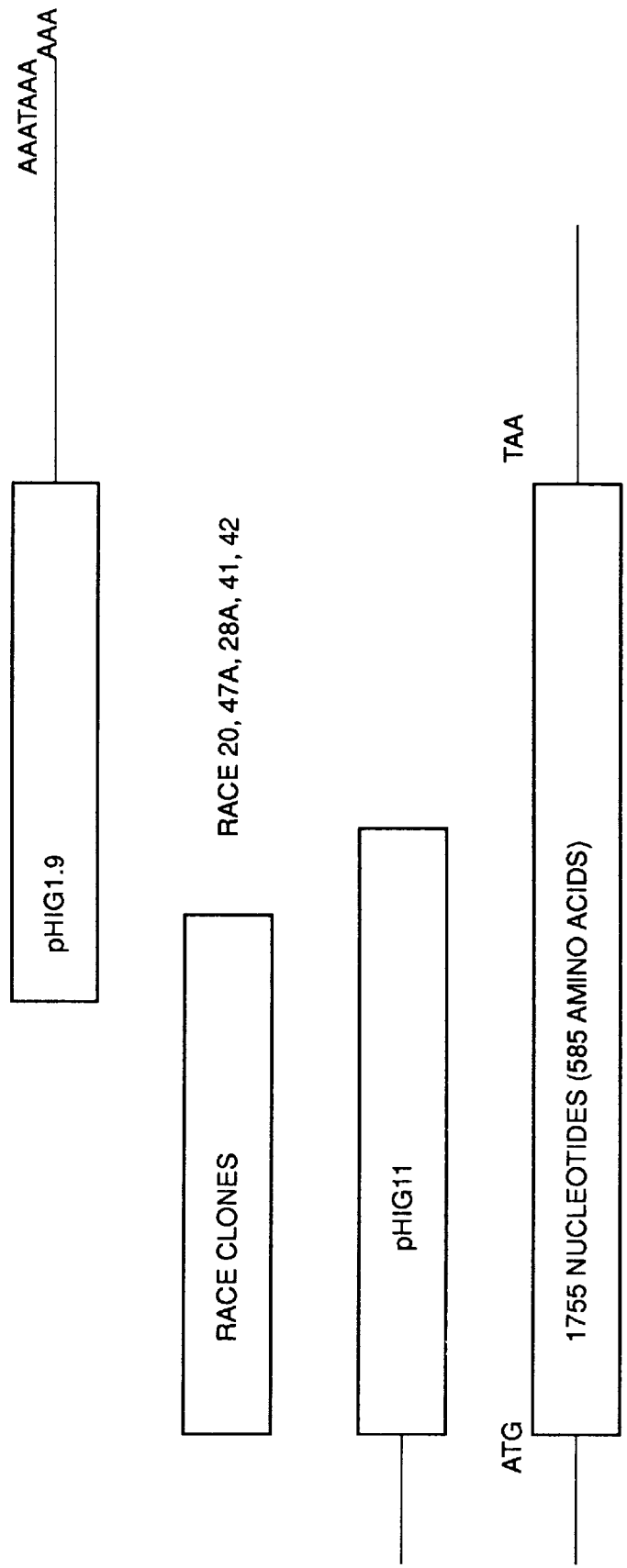
FIG. 1 is a diagram of partial human islet GAD clones.

Human pancreatic islet cell GAD is an enzyme that catalyzes the synthesis of GABA. The present invention provides isolated nucleotide sequences of human islet cell GAD, thereby providing for the ultimate expression of human islet cell GAD polypeptides. Recombinant DNA expression systems provide convenient means for obtaining large quantities of recombinant human islet cell GAD and fragments thereof in relatively pure form.

The invention also provides recombinant human islet cell GAD polypeptides. By "recombinant" is meant a polypeptide produced by a recombinant expression system and typically free of native endogenous substances. By "polypeptide" is meant to include sequences of at least about six amino acids, typically 10 to 25, and up to 100–200 amino acids or more, including up to the entire human islet GAD protein. When the polypeptide comprises the entire GAD protein, the polypeptides will be substantially homologous to the entire human islet cell GAD sequence as disclosed in SEQ. ID. NO. 1 and FIGS. 2a–2e. By "substantially homologous" is meant to include sequences which have at least about 85% homology, preferably at least 90%, and more preferably at least about 95% or more homology to the amino acid sequence of the human islet cell GAD sequence (s) of the invention and still retain at least some biological activity of the native GAD. By "biological activity" is meant the ability to catalyze the decarboxylation of L-glutamic acid, to specifically bind antibodies which bind to the native human islet cell GAD protein (i.e., autoantibodies to human islet cell GAD), and/or to elicit antibodies which also bind to the native protein.

When the polypeptide of the invention comprises less than the entire GAD protein, the polypeptide will preferably be substantially homologous to a portion of at least about 6, sometimes 10, more usually at least about 15 amino acids of a variable region of the GAD protein. That is, certain sequence domains are variable, differing at least about 15%, more typically at least about 20%, from analogous regions of GADs of other tissues and/or species, while other regions of the human islet cell GAD are identical or nearly identical to other GADS, and thus represent conserved regions. The conserved and variable sequence regions of the human islet cell GAD of the present invention can be determined by techniques known to the skilled artisan, such as sequence alignment techniques, e.g., using the Sequence Analysis Software Package of the Genetics Computer Group, University of Wisconsin Biotechnology Center, 1710 University Avenue, Madison, Wis. 53705 (Devereux, *Nuc. Acids. Res.* 12:387–396 (1984). Homology is determined by attaining optimal alignment of the present GAD sequence with, e.g., brain GAD sequences of rat and cat, as disclosed in Julien et al., *J. Neurochem.* 54:703–705 (1990), incorporated herein by reference.

For example, in reference to FIGS. 2a–2e, human islet GAD variable region domains, when compared to the amino acid sequence of cat and rat, are identified at the N-terminal residues 1–91, and at positions 137–171, 405–431, and 511–540. Epitopes which comprise at least a portion of variable region domain, typically at least about six contiguous amino acids from the variable region and often ten or more residues, may serve as human islet cell GAD-specific markers.

As will be appreciated by those skilled in the art, the invention also includes those polypeptides having slight variations in amino acid sequences or other properties. Such variations may arise naturally as allelic variations (e.g., due to genetic polymorphism) or may be produced by human intervention (e.g., by mutagenesis of cloned DNA sequences), such as induced point, deletion, insertion and substitution mutants. Minor changes in amino acid sequence are generally preferred, such as conservative amino acid replacements, small internal deletions or insertions, and additions or deletions at the ends of the molecules. Substitutions may be designed based on, for example, the model of Dayhoff, et. al. (in *Atlas of Protein Sequence and Structure* 1978, Nat'l Biomed. Res. Found., Washington, D.C.). These modifications can result in changes in the amino acid sequence, provide silent mutations, modify a restriction site, or provide other specific mutations. The polypeptides may comprise one or more selected antigenic determinants of human islet GAD, possess catalytic activity exhibited by native GAD protein or alternatively lack such activity, mimic GAD binding regions, or the like.

Nucleic acid sequences encoding human islet cell GAD as described herein can be cloned directly from human cell sources that express the enzyme. Preferred sources include human pancreatic islet cells, but neurons which secrete GABA may also serve as a source for the homologous human brain GAD. The nucleotide and amino acid sequences provided by the present invention can also be used to identify and clone other tissue specific human GADs, as described further below. Useful nucleic acid sequences for cloning and expressing GAD sequences include mRNA, genomic DNA and cDNA, although for expression cDNAs are generally preferred because they lack introns that may interfere with expression.

To obtain a human islet GAD clone or other human GAD clone which is substantially homologous to the human islet GAD, a cDNA library prepared from, e.g., human pancreatic islet cells, is screened with labeled probes from the human islet GAD sequences provided herein, or from homologous sequence regions of, e.g., mouse brain GAD (Katarova et al., *Eur. J. Neurosci.* 2:190–202 (1990)), cat brain GAD (Kobayashi et al. *J. Neurosci.* 7:2768–2772 (1987)), or rat brain GAD (Julien et al., *J. Neurochem.* 54:703–705 (1990)), each of which is incorporated herein by reference. An oligo-dT primed cDNA library can be constructed with polyA$^+$ RNA purified from human pancreatic islet cells or from other tissues/cells as desired. The library is screened with, e.g., antibodies to homologous GAD and/or labeled probes. Partial clones may be used as probes in additional screening until the complete coding sequence is obtained. If necessary, partial clones are joined in the correct reading frame to construct the complete coding sequence. Joining is achieved by digesting clones with appropriate restriction endonucleases and joining the fragments enzymatically in the proper orientation. Depending on the fragments and the particular restriction endonucleases chosen, it may be necessary to remove unwanted DNA sequences through a "loop out" process of deletion mutagenesis or through a combination of restriction endonuclease cleavage and mutagenesis. It is preferred that the resultant sequence be in the form of a continuous open reading frame, that is, that it lack intervening sequences (introns).

Representative human cDNA islet GAD clones isolated as described herein can be combined to give the full coding sequence for the human islet cell GAD. For example, two clones, designated pHIG1.9 and pHIG11, are combined to give the full coding sequence and 3'-untranslated sequences, as shown in FIGS. 2a–2e, SEQ. ID. NO. 1. This clone has a polyadenylation sequence upstream of a poly A sequence at the 3' end. It will be readily understood by those skilled in the art that due to the degeneracy of the code, there can be considerable variation in a nucleotide sequence which encodes the same amino acid sequence, or which sequence encodes a mutant sequence which varies from a reference sequence, such as that of SEQ. ID. NO 1 and FIGS. 2a–2e. In the case of a mutant sequence, which mutant should be substantially homologous to at least a portion of the reference sequence, the net effect of the mutation(s) should not produce adverse functional differences between the native and the mutant sequences. The identity of a human islet GAD clone can be confirmed by, for example, in vitro translation and subsequent immunoreactivity and migration on an SDS-polyacrylamide gel, sequencing, or by appropriate enzymatic activity, e.g., catalyzing the synthesis of γ-aminobutyric acid. GAD catalytic activity can be assayed by $CO_2$ and/or GABA methods as described in, e.g., Chude and Wu, *J. Neurochem.* 27:83–86 (1976). Briefly, the assays can employ, e.g., L-[U-$^{14}$C]glutamate as a substrate and the amounts of $^{14}CO_2$ and [$^{14}$C]GABA formed are determined.

With the nucleotide and deduced amino acid sequences of human islet GAD provided herein, genomic or cDNA sequences encoding other human GADs may be obtained from libraries prepared from other cells and tissues according to known procedures. For instance, using oligonucleotide probes derived from human islet cell GAD sequences, generally of at least about fourteen nucleotides and up to twenty-five or more nucleotides in length, DNA sequences encoding GADs of other cells, such as isozymes from beta cells, testis, or neurons, may be obtained. Again, if partial clones are obtained, it is necessary to join them in proper reading frame to produce a full length clone, using such techniques as endonuclease cleavage, ligation and loopout mutagenesis.

For expression, a DNA sequence encoding human islet GAD is inserted into a suitable expression vector, which in turn is used to transform or transfect appropriate host cells for expression. Expression vectors for use in carrying out the present invention will comprise a promoter capable of directing the transcription of a cloned DNA and a transcriptional terminator, operably linked with the sequence encoding the human islet GAD so as to produce a continuously transcribable gene sequence which produces sequences in reading frame and continuously translated to produce a human islet GAD polypeptide.

Host cells for use in practicing the present invention include mammalian, avian, plant, insect, bacterial and fungal cells, but preferably eukaryotic cells. Preferred eukaryotic cells include cultured mammalian cell lines (e.g., rodent or human cell lines, but most preferably human) and fungal cells, including species of yeast (e.g., Saccharomyces spp., particularly *S. cerevisiae*, Schizosaccharomyces spp., or Kluyveromyces spp.) or filamentous fungi (e.g., Aspergillus spp., Neurospora spp.). Methods for producing recombinant polypeptides in a variety of prokaryotic and eukaryotic host cells are generally known in the art.

To produce the recombinant human islet GAD polypeptides of the invention in mammalian cells, a variety of host cells may be used. Cultured mammalian cells for use in the present invention include COS-1 (ATCC CRL 1650), BALB/c 3T3 (ATCC CRL 163), BHK (ATCC CRL 10314), 293 (ATCC CRL 1573), Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), Mouse liver (ATCC CCL 29.1), NCTC 1469 (ATCC CCL 9.1) and DUKX cells (Urlaub and Chasin, *Proc. Natl. Acad. Sci. USA* 77: 4216–4220, 1980). Beta-cell lines, such as those of rat (RIN-5AH-B; Karlsen, et. al., *J. Biol. Chem.* 266:7542–7548, (1991)), mouse (NIT; Hamaguchi et al., *Diabetes* 39:415–425 (1990)) and hamster (HIT; Santerre, et. al., *Proc. Natl. Acad. Sci. USA* 78:4339–4343 (1981)) may also be used.

Mammalian expression vectors for use in carrying out the present invention will include a promoter capable of directing the transcription of a cloned gene or cDNA. Preferred promoters include viral promoters and cellular promoters. Viral promoters include the immediate early cytomegalovirus promoter (Boshart et al., *Cell* 41: 521–530, 1985), the SV40 promoter (Subramani et al., *Mol. Cell. Biol.* 1: 854–864, 1981), and the major late promoter from Adenovirus 2 (Kaufman and Sharp, *Mol. Cell. Biol.* 2: 1304–1319, 1982). Cellular promoters include the mouse metallothionein-1 promoter (Palmiter et al., U.S. Pat. No. 4,579,821), a mouse $V_K$ promoter (Bergman et al., *Proc. Natl. Acad. Sci. USA* 81: 7041–7045, 1983; Grant et al., *Nuc. Acids Res.* 15: 5496, 1987) and a mouse $V_H$ promoter (Loh et al., *Cell* 33: 85–93, 1983). Also contained in the expression vectors is a polyadenylation signal located downstream of the coding sequence of interest. Polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9: 3719–3730, 1981). Vectors can also include enhancer sequences, such as the SV40 enhancer and the mouse μ enhancer (Gillies, *Cell* 33: 717–728, 1983). Expression vectors may also include sequences encoding the adenovirus VA RNAs. Vectors can be obtained from commercial sources (e.g., Stratagene, La Jolla, Calif.).

Cloned DNA sequences may be introduced into cultured mammalian cells by a variety of means, as will be recognized by those skilled in the art. For example, calcium phosphate-mediated transfection (Wigler et al., *Cell* 14: 725, 1978; Corsaro and Pearson, *Somatic Cell Genetics* 7: 603, 1981; Graham and Van der Eb, *Virology* 52: 456, 1973), electroporation (Neumann et al., *EMBO J.* 1: 841–845, 1982), or DEAE-dextran mediated transfection (Ausubel et al., (ed.) *Current Protocols in Molecular Biology*, John Wiley and Sons, Inc., NY (1987), incorporated herein by reference) may find convenient use. To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. Further, the selectable marker may be an amplifiable selectable marker, and preferred amplifiable selectable markers include the DHFR gene and the neomycin resistance gene. Selectable markers are reviewed by Thilly (*Mammalian Cell Technology*, Butterworth Publishers, Stoneham, Mass., which is incorporated herein by reference). The choice of selectable markers is well within the level of ordinary skill in the art.

Selectable markers may be introduced into the cell on a separate vector at the same time as the islet cell GAD sequence of interest, or they may be introduced on the same vector. If on the same vector, the selectable marker and the islet cell GAD sequence of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA" to the mixture which is introduced into the cells.

Transfected mammalian cells are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable selectable marker the drug concentration may be increased in a stepwise manner to select for increased copy number of the cloned sequences, thereby increasing expression levels.

Promoters, terminators and methods for introducing expression vectors encoding foreign proteins such as human islet GAD into plant, avian and insect cells are well known in the art. The use of baculoviruses, for example, as vectors for expressing heterologous DNA sequences in insect cells has been reviewed by Atkinson et al. (*Pestic. Sci.* 28: 215–224,1990). The use of *Agrobacterium rhizogenes* as vectors for expressing genes in plant cells has been reviewed by Sinkar et al. (*J. Biosci.* (Bangalore) 11: 47–58, 1987).

Techniques for transforming fungi are well known in the literature, and have been described, for instance, by Beggs (*Nature* 275:104–108 (1978)), Hinnen et al. (*Proc. Natl. Acad. Sci. USA* 75: 1929–1933, 1978), Yelton et al. (*Proc. Natl. Acad. Sci. USA* 81: 1740–1747, 1984), Russell (*Nature* 301: 167–169, 1983) and U.S. Pat. No. 4,935,349, incorporated herein by reference. The genotype of the host cell will generally contain a genetic defect that is complemented by the selectable marker present on the expression vector. Choice of a particular host and selectable marker is well within the level of ordinary skill in the art.

Suitable yeast vectors for use in the present invention include YRp7 (Struhl et al., *Proc. Natl. Acad. Sci. USA* 76: 1035–1039, 1978), YEp13 (Broach et al., *Gene* 8: 121–133, 1979), POT vectors (Kawasaki et al, U.S. Pat. No. 4,931, 373, which is incorporated by reference herein), pJDB249 and pJDB219 (Beggs, ibid.) and derivatives thereof. Such vectors will generally include a selectable marker, which may be one of any number of genes that exhibit a dominant phenotype for which a phenotypic assay exists to enable transformants to be selected. Preferred selectable markers are those that complement host cell auxotrophy, provide antibiotic resistance or enable a cell to utilize specific carbon sources, and include LEU2 (Broach et al., ibid.), URA3 (Botstein et al., *Gene* 8: 17, 1979), HIS3 (Struhl et al., ibid.) or POT1 (Kawasaki et al., ibid.). Another suitable selectable marker is the CAT gene, which confers chloramphenicol resistance on yeast cells.

Preferred promoters for use in yeast include promoters from yeast glycolytic genes (Hitzeman et al., *J. Biol. Chem.* 255: 12073–12080, 1980; Alber and Kawasaki, *J. Mol. Appl. Genet.* 1: 419–434, 1982; Kawasaki, U.S. Pat. No. 4,599, 311) or alcohol dehydrogenase genes (Young et al., in *Genetic Engineering of Microorganisms for Chemicals*, Hollaender et al., (eds.), p. 355, Plenum, New York, 1982; Ammerer, *Meth, Enzymol.* 101: 192–201, 1983). In this regard, particularly preferred promoters are the TPI1 promoter (Kawasaki, U.S. Pat. No. 4,599,311, 1986) and the ADH2-4$^C$ promoter (Russell et al., *Nature* 304: 652–654, 1983; Irani and Kilgore, U.S. patent application Ser. No. 183,130, which is incorporated herein by reference). The expression units may also include a transcriptional terminator. A preferred transcriptional terminator is the TPI1 terminator (Alber and Kawasaki, ibid.).

Additional vectors, promoters and terminators which can be used in expressing the human islet GAD of the invention in yeast are well known in the art and are reviewed by, for example, Emr, *Meth. Enzymol.* 185:231–279, (1990), incorporated herein by reference.

Host cells containing DNA constructs of the present invention are then cultured to produce the human islet cell GAD polypeptides. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct by, for example, drug selection or deficiency in an essential nutrient which is complemented by the selectable marker on the DNA construct or co-transfected with the DNA construct. Selection of a medium appropriate for the particular cell line used is within the level of ordinary skill in the art.

For instance, yeast cells are preferably cultured in a medium which comprises a nitrogen source (e.g., yeast extract), inorganic salts, vitamins and trace elements. The pH of the medium is preferably maintained at a pH greater than 2 and less than 8, preferably at pH 5–6. Methods for maintaining a stable pH include buffering and constant pH control, preferably through the addition of sodium hydroxide. Preferred buffering agents include succinic acid and Bis-Tris (Sigma Chemical Co., St. Louis, Mo.). Cultured mammalian cells are generally cultured in commercially available serum-containing or serum-free media.

The human islet cell GAD produced according to the present invention may be purified by affinity chromatography on an antibody column using antibodies, preferably monoclonal antibodies, directed against GAD. Additional purification may be achieved by conventional chemical purification means, such as liquid chromatography, gradient centrifugation, and gel electrophoresis, among others. Methods of protein purification are known in the art (see generally, Scopes, R., *Protein Purification*, Springer-verlag, NY (1982), which is incorporated herein by reference) and may be applied to the purification of the recombinant human islet GAD described herein. Substantially pure recombinant human islet GAD of at least about 50% is preferred, at least about 70–80% more preferred, and 95–99% or more homogeneity most preferred, particularly for pharmaceutical uses. Once purified, partially or to homogeneity, as desired, the recombinant human islet GAD may then be used diagnostically, therapeutically, etc. as further described herein below.

Human islet GAD polypeptides can also be produced by fragmenting larger purified recombinant GAD polypeptides with a protease or a chemical agent, or by producing recombinant polypeptide fragments. Synthetic islet cell GAD peptides can also be produced from the amino acid sequences provided herein, using conventional solid-phase synthesis procedures as described in, e.g., Merrifield, *Fed. Proc.* 21:412 (1962) and Barany and Merrifield, in *The Peptides*, Vol. 2, pp. 1–284 (1979) Academic Press, NY, which are incorporated herein by reference. Short polypeptide sequences, or libraries of overlapping peptides, usually from about 6 up to about 35 amino acids, which correspond to selected human islet GAD regions can be readily synthesized and then screened in screening assays designed to identify peptides having a desired activity, such as domains which are responsible for or contribute to GAD catalytic activity, binding activity, immunodominant epitopes (particularly those recognized by autoantibodies), and the like. Recombinant polypeptides can be produced by expressing GAD DNA fragments, such as fragments generated by digesting a human islet cell GAD cDNA at convenient restriction sites. The isolated recombinant polypeptides or cell-conditioned media are then assayed for activity as described above.

Human islet cell GAD polypeptides produced according to the present invention have a variety of uses. For example, recombinant or synthetic GAD polypeptide compositions can be used diagnostically, in the detection and quantitation of anti-GAD autoantibodies or detecting free GAD (as a measure of beta cell destruction) in a biological sample, that is, any sample derived from or containing cells, cell components or cell products, including, but not limited to, cell culture supernatants, cell lysates, cleared cell lysates, cell extracts, tissue extracts, blood, plasma, serum, and fractions thereof. By means of having human islet GAD polypeptides which specifically bind to human islet GAD autoantibodies, the concentration of the autoantibodies in an individual can be measured, which level can then be used to monitor the progression or regression of the potentially harmful autoantibodies in individuals at risk. The assay results can also find use in monitoring the effectiveness of therapeutic measures for treatment of IDDM, Stiff-man Syndrome, or related diseases.

As will be recognized by those skilled in the art, numerous types of immunoassays are available for use in the present invention. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988), each incorporated by reference herein. In one assay format anti-human islet GAD autoantibodies in a biological sample are quantified directly by measuring the binding of antibodies to recombinant or synthetic GAD polypeptides. The biological sample is contacted with at least one human islet cell GAD polypeptide of the invention under conditions conducive to immune complex formation. The immune complexes formed between the GAD polypeptide and the antibodies are then detected and the presence of the autoantibodies to human islet cell GAD in the sample determined. The immune complexes can be detected by means of, e.g., labeled antibodies, such as anti-IgG, IgM and/or IgA human antibodies, or antibodies which bind to the human GAD. Separation steps (e.g., washes) may be necessary in some cases to distinguish specific binding over background. In another format, a patient's antibodies or serum GAD can be measured by competing with labeled or unlabeled antibodies to GAD or GAD polypeptides, respectively, for binding. Unlabeled GAD may be used in combination with labeled antibodies which bind to human antibodies or to GAD. Alternatively, the GAD polypeptide may be directly labeled. A wide variety of labels may be employed, such as radionuclides, particles (e.g., gold, ferritin, magnetic particles, red blood cells), fluors, enzymes, enzyme substrates, enzyme cofactors enzyme inhibitors, ligands (particularly haptens), chemiluminescers, etc.

Thus, autoantibodies to β-islet cell GAD autoantigens may be identified and, if desired, extracted from patient's serum by binding to the GAD. The GAD polypeptide may be attached, e.g., by absorption, to an insoluble or solid support, such as an ELISA microtiter well, microbeads, filter membrane, insoluble or precipitable soluble polymer, etc. to function as an affinity resin. The captured autoantibodies may then be identified by several methods. For example, antisera or monoclonal antibodies to the antibodies may be used. These antisera or monoclonal antibodies are typically non-human in origin, such as rabbit, goat, mouse, etc. These anti-antibodies may be detected directly if attached to a label such as $^{125}$I, enzyme, biotin, etc., or may be detected indirectly by a labeled secondary antibody made to specifically detect the anti-antibody.

Kits can also be supplied for use with the recombinant or synthetic human islet GAD polypeptides in detecting autoantibodies to pancreatic β-islet cells. Thus, the subject GAD polypeptide compositions of the present invention may be provided, usually in lyophilized form, in a container, either alone or in conjunction with additional reagents, such as GAD-specific antibodies, labels, and/or anti-human antibodies, and the like. The GAD polypeptide and antibodies, which may be conjugated to a label, or unconjugated, and are included in the kits with buffers, such as Tris, phosphate, carbonate, etc., stabilizers, biocides, inert proteins, e.g., serum albumin, or the like. Frequently it will be desirable to include an inert extender or excipient to dilute the active ingredients, where the excipient may be present in from about 1 to 99% of the total composition. Where an antibody capable of binding to the islet GAD autoantibody or to the recombinant or synthetic GAD is employed in an assay, this will typically be present in a separate vial.

Antibodies for diagnostic or therapeutic uses which bind human islet GAD and/or islet cell GAD polypeptides of the invention can be produced by a variety of means. The production of non-human monoclonal antibodies, e.g., murine, is well known and may be accomplished by, for example, immunizing the animal with a recombinant or synthetic GAD molecule or a selected portion thereof (e.g., a peptide). For example, by selected screening one can identify a region of the GAD molecule such as that predominantly responsible for recognition by anti-GAD autoantibodies, or a portion which comprises an epitope of an islet cell GAD variable region, which may thus serve as an islet cell GAD-specific marker. Antibody producing cells obtained from the immunized animals are immortalized and screened, or screened first for, e.g., the production of antibody which inhibits the interaction of the anti-GAD autoantibody with the GAD molecule and then immortalized. As the generation of human monoclonal antibodies to a human antigen, such as the human islet cell GAD molecule, may be difficult with conventional immortalization techniques, it may be desirable to first make non-human antibodies and then transfer via recombinant DNA techniques the antigen binding regions of the non-human antibodies, e.g. the F(ab')$_2$ or hypervariable regions, to human constant regions (Fc) or framework regions to produce substantially human molecules. Such methods are generally known in the art and are described in, for example, U.S. Pat. No. 4,816,397, EP publications 173,494 and 239,400, which are incorporated herein by reference. Alternatively, one may isolate DNA sequences which encode a human monoclonal antibody or portions thereof that specifically bind to the human islet cell GAD protein by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

Antibodies which bind to the recombinant human islet cell GAD, including those antibodies which inhibit the binding of autoantibodies to the human islet cell GAD autoantigen can also be used in the generation of anti-idiotype antibodies. Anti-idiotype antibodies may be produced by, for example, immunizing an animal with the primary antibody or with the antigen binding fragment thereof. Those anti-idiotype antibodies whose binding to the primary antibody is inhibited by the human islet cell GAD molecule are selected. Since both the anti-idiotype antibody and the GAD molecule bind to the primary antibody, the anti-idiotype antibody may represent the "internal image" of an epitope and thus may substitute for the GAD autoantigen and inhibit disease by blocking the GAD autoantibodies. Treatment of autoimmune diseases with intravenous immunoglobulin preparations containing anti-idiotype antibodies is disclosed by, for example, Nydegger, et. al., (*Clin. Immunol. Immunopathol.* 53 (2 part 2):572–82 (1989)).

In another aspect of the invention, the human islet GAD polypeptides of the invention can be used to clone T cells which have specific receptors for GAD molecules. Once the GAD-specific T cells are isolated and cloned using techniques generally available to the skilled artisan, the T cells or membrane preparations thereof can be used to immunize animals to produce antibodies to the islet GAD receptors on T cells. The antibodies can be polyclonal or monoclonal. If polyclonal, the antibodies and can be murine, lagomorph, equine, ovine, or from a variety of other mammals. Monoclonal antibodies will typically be murine in origin, produced according to known techniques, or human, as described above, or combinations thereof, as in chimeric or humanized antibodies. The anti-GAD receptor antibodies thus obtained can then be administered to patients to reduce or eliminate T cell subpopulations which recognize and participate in the immunological destruction of GAD-bearing cells in an individual predisposed to or already suffering from the disease. Further, the GAD-specific T cell receptors can thus be identified, cloned and sequenced, and receptor polypeptides synthesized which bind to the GAD molecules and block recognition of the GAD-bearing cells, thereby impeding the autoimmune response against host islet cells. Howell et al. (*Science* 246:668–670 (1989)) have demonstrated that T cell receptor peptides can block the formation of the tri-molecular complex between T cells, autoantigen and major histocompatibility complex in an autoimmune disease model.

In other embodiments the invention concerns human islet GAD polypeptides which inhibit the binding of autoantibodies to human GAD islet cell autoantigen and inhibit the proliferation of T cells. The portion(s) of the GAD autoantigen protein which binds the auto-antibodies may be identified using relatively short fragments of GAD islet polypeptides, as generally described above, and determining which fragment(s) binds to the autoantibodies, particularly those autoantibodies associated with IDDM or related disease, such as those antibodies isolated from a patient using plasmapheresis as discussed below.

Thus, in another aspect of the invention the human islet cell GAD polypeptides can be used in immunoadsorptive plasmapheresis therapy to remove autoantibodies from the circulation of an individual. An individual undergoing such treatment will typically have detectable levels of anti-GAD autoantibodies and thus will be at risk of developing disease associated with such autoantibodies, such as IDDM or Stiff-man syndrome, or will already be afflicted by such disease. The plasmapheresis treatment is provided by removing the patient's blood, separating the blood cells therefrom, treating the separated plasma in, e.g., an immunoadsorbent column to remove the autoantibodies, and mixing and returning the treated plasma and blood cells directly to the patient. Typically the patient's blood is removed, treated and returned to the patient in a continuous manner.

The immunoadsorbent column for treating the plasma will comprise a recombinant islet cell GAD as described herein, covalently coupled to a solid-phase matrix. Means for coupling polypeptides to various solid-phase matrices are generally known in the art. Typically the covalent coupling, which can include a "spacer" molecule, as described in e.g., U.S. Pat. No. 4,685,900, which is incorporated herein by reference, is accomplished by appropriately derivatizing the solid-phase matrix and linking the protein under conditions which maximize the binding activity and capacity of the GAD polypeptide of the invention. Desirably, the immunoadsorbent thus formed has a high capacity for adsorption of the autoantibodies, is highly stable and is not released into the plasma. The volume of plasma which is treated and the frequency of treatment will depend on, e.g., the severity of the disease being treated, the quantity of autoantibodies in a patient's plasma, the overall health and condition of the patient, and the judgment of the attending physician. In any event, the treatment should be sufficient to prevent or alleviate the symptoms or arrest development of the disease.

The human islet cell GAD polypeptides of the invention can also be used to induce immunological tolerance or nonresponsiveness (anergy) to GAD autoantigen in patients predisposed or already mounting an immune response to GAD autoantigen of the islet β-cells. The use of polypeptide antigens in the suppression of autoimmune disease is disclosed by Wraith, et. al., (*Cell* 59:247–255, (1989)). Tolerance can be induced in both adults and neonates, although conditions for inducing such tolerance will vary according to a variety of factors. In a neonate, tolerance can be induced by parenteral injection of GAD antigen, either with recombinant polypeptide or synthetic antigen, or more conveniently by oral administration in an appropriate formulation. The precise amount of administration, its mode and frequency of dosages will vary.

To induce immunological tolerance to the GAD autoantigen in an adult susceptible to or already suffering from a GAD related disease such as IDDM, the precise amounts and frequency of administration will also vary, but for adults will generally range from about 1 to 1,000 mg/kg, preferably about 10–100 mg/kg, administered daily or from one to several times per week, and will be administered by a variety of routes, such as parenterally, orally, by aerosol, intradermal injection, etc., but preferably by intravenous infusion. For neonates the doses will generally be higher than those administered to adults; e.g., typically from about 100 to 1,000 mg/kg. To induce tolerance with lower doses of antigen (a "low zone tolerance") co-administration of an immunosuppressive drug, such as cyclophosphamide or, preferred for use in children, azathioprine, may be necessary during the low dose antigen treatment to inhibit antibody synthesis.

The GAD polypeptides will typically be more tolerogenic when administered in a soluble form rather than an aggregated or particulate form. Persistence of a GAD polypeptide antigen of the invention is generally needed to maintain tolerance in an adult, and thus may require more frequent administration of the antigen, or its administration in a form which extends the half-life of the GAD islet cell polypeptide.

The following examples are offered by way of illustration, not by limitation.

EXAMPLE I

Cloning and Sequencing of Human Islet Cell GAD

Islet cells were isolated from human pancreata obtained from organ transplant donors for whom a matched recipient was not available. After in situ perfusion with cold UW solution (Du Pont, Boston, Mass.), each pancreas was carefully excised, the pancreatic duct cannulated, and 4 mg/ml collagenase solution (Type V, Sigma, St. Louis, Mo.) infused at a constant rate, first at 4° C. and then 39° C. The gland was teased apart, and liberated fragments were washed by centrifugation, triturated through needles of decreasing caliber, and purified by discontinuous Ficoll density centrifugation (G. L. Warnock, *Diabetes* 35: Suppl. 1, pp. 136–139, January 1989). Material harvested from the upper interfaces was pooled and counted after a determination of islet purity by dithiazone staining. Islets used in library construction were greater than 65% pure, while islets used in Northern blots were greater than 40% pure. The average islet diameter was 175 μm. Additionally, the isolated islets showed both first and second phase insulin secretory function after perfusion with either high glucose or with isobutylmethylxanthine (IBMX).

Poly(A)+RNA was isolated using the FastTrack™ mRNA isolation kit (Invitrogen, San Diego, Calif.) according to the manufacturer's instructions. Briefly, 30,000 purified islets were quickly lysed in lysis buffer, homogenized using needles of decreasing caliber, and digested in the presence of proteinase K and RNasin, then poly(A)+RNA was selected by oligo-d(T) cellulose chromatography. The concentration and purity of the eluted fractions were determined at $OD_{260/280}$.

Approximately 2.5 μg poly(A)+RNA from the human islets was used for cDNA library construction using a Librarian R II cDNA library construction system (Invitrogen) and Electromax™ DH10B *E. coli* cells (GIBCO BRL, Gaithersburg, Md.) according to the manufacturers' instructions. In short, approximately 2.5 μg of poly(A)+RNA, isolated from human islets, was converted into double-stranded cDNA, followed by the addition of BstX I nonpalindromic linkers (Invitrogen). The cDNA was size fractionated, and the unreacted linkers were removed by agarose gel electrophoresis and electroelution. Complementary DNA strands larger than 600 bp were selected and ligated into the Librarian R II pcDNA II vector. Following electroporation of a fraction of the ligated material into DH 10B *E. coli* cells, a total of $2 \times 10^6$ colonies with a background of approximately 10% was screened by hybridization. These colonies were replicated in duplicate to nylon filters, lysed, neutralized, washed and baked essentially as described by Sambrook et al., *Molecular Cloning, A Laboratory Manual*, Cold Spring Harbor Press, Cold Spring Harbor, N.Y. (1989), incorporated herein by reference.

To identify colonies containing human islet GAD cDNA, 20-mer oligonucleotide probes representing conserved regions from three different homologous nucleotide sequences of the internal as well as the N- and C-terminal parts of the coding regions of cat (Kobayashi, et al. *J. Neurosci.* 7:2768–2772 (1987)), rat (Julien et al., *J. Neurochem.* 54:703–705 (1990)), and mouse (Katarova, et al. ibid.) brain GAD were synthesized (Table 1), $^{32}$P-ATP labeled by kinasing and used to screen the nylon filter replicas of the human islet cDNA library. Following hybridization and consecutive washings at increasing stringency, six positive colonies representing insert sizes from 0.7 to 1.4 kb were selected for colony purification and subsequent sequence analysis. By rescreening the library with a 600 bp PvuII-PstI fragment of a circa 1300 bp clone containing 1281 base pairs of the 3' coding sequence (pHIG1.3), another clone, pHIG1.9, FIG. 1, with a 1.9 kb insert, was isolated.

TABLE 1

```
SEQ. ID. NO. 3   5'-GCGGGAGCGGATCCTAATACTACCAACCTGCG-3'  ZC3338
     5'probe SEQ. ID. NO. 4   5'-ACCATGGTTGTTCCTGACTCCATCAT-3'  ZC3339
     3'probe SEQ. ID. NO. 5   5'-CTGACATCAACTGCCAATACCAATATGTTCACATATGAAA-
     TTGCA-3'    ZC3337    main probe, primary screen
```

For DNA sequencing, plasmids were isolated from positive clones by the rapid boiling method (Homes and Quigley, *Anal. Biochem.* 114:193–197 (1981). The resulting double-stranded cDNA was sequenced using the Sequenase® kit (version 2.0, United States Biochemical, Cleveland, Ohio) with primers hybridizing to the flanking SP6 and T7 promoters. As the sequencing progressed, new primers representing 20-mer 3' oligonucleotides of the insert were synthesized and used to obtain the entire sequence of the human islet GAD cDNA inserts. The nucleotide sequences were analyzed with the sequence analysis software package of the University of Wisconsin genetics computer group (Devereux, *Nuc. Acids. Res.* 12:387–396, (1984), incorporated herein by reference).

To obtain full-length clones, the 5' cDNA ends of two clones were extended using a variation of the PCR-RACE protocol (Frohman et al., *Proc. Natl. Acad. Sci. USA* 85: 8998–9002, 1988). Oligonucleotide primers (ZC3614, ZC3623, Table 2) complementary to a region near the 5' end of GAD clones, and containing adapter sequences with an Eco RI restriction site, were annealed with an aliquot of islet cell poly(A)$^+$ RNA. Following extension, the products were terminal deoxynucleotidyltransferase-tailed with dGTP, and a poly-dCTP primer with an Eco RI adapter (ZC2488, Table 2) was used on second strand synthesis to generate a cDNA population enriched for GAD but still heterogeneous due to non-specific pairing of the internal primer. As a second step, a second oligonucleotide complementary to a region upstream from the internal primer (ZC3746 upstream of ZC3614 or ZC3745 upstream of ZC3623; Table 2), was used to prime the minus strand while a primer complementary to the Eco RI adapter (ZC2633; Table 2) was used to prime the plus strand. PCR amplification yielded further enrichment of GAD sequences. Using the GeneAmp PCR kit (Perkin-Elmer Cetus, Norwalk, Conn.), the reaction was cycled 40 times at 94° C. for 1 minute to denature, 50° C. for 2 minutes and 72° C. for 2 minutes. The resulting products were electrophoresed on an agarose gel, and the GAD sequences were eluted, digested with Eco RI and cloned into the vector pUC19.

(FIGS. 2a–2e). PHIG 11 extended the 5' end of the cDNA sequence to 250 bp upstream from the predicted N-terminal Met. pHIG1.1 contains an intron as a cloning intron from an aberrantly spliced RNA.

The human islet GAD cDNA nucleotide sequence had a overall homology of only about 70% to the brain GAD cDNA sequences of the rat, cat and mouse, whereas the brain sequences showed about 91% homology among the three. The predicted amino acid sequence homology between the human islet GAD and those of the brain sequences of cat, rat and mouse is about 76%, again in contrast to the more than about 98% homology found among the brain GAD amino acid sequences. Comparison of the 5'-end of the human islet sequence to the 68 amino acid 5'-end of the human testis GAD (Perrson et al., *Mol. Cell. Biol.* 10:4701–4711 (1990)) shows differences at 15 amino acid positions, whereas only two amino acid substitutions have been found between the human testis sequence and rat brain GAD.

Figure 3:
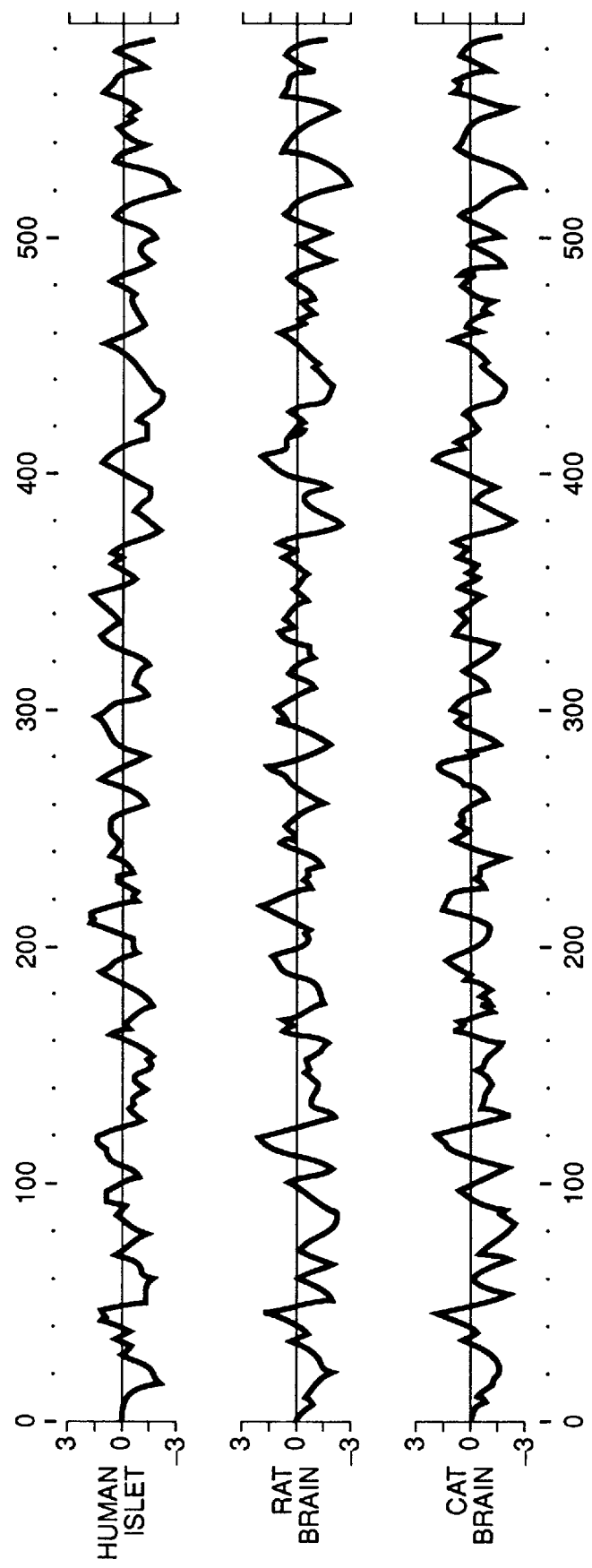
FIG. 3 is a hydropathy plot of human islet GAD and rat and cat brain GAD.

A hydropathy plot of the human islet GAD primary structure indicated regions of increased hydrophobicity when compared to rat and cat brain GAD (FIG. 3). Apart from N-terminal end differences, the sequences at amino acid positions 165–195 were particularly different. The hydropathy plot analysis suggests that the human islet GAD has features which are distinct from the rat and mouse brain GAD sequences.

TABLE 2

| | | |
|---|---|---|
| SEQ. ID. No. 6 | 5'-AAATGAGAATTCACACGCCGGCAGCAGGTC-3' | ZC3614 |
| SEQ. ID. No. 7 | 5'-AAGGAATTCAAGTTGATTGAAGTATCT-3' | ZC3623 |
| SEQ. ID. No. 8 | 5'-GGCGAATTCGCATATTTTAGAGTTGTTTGG-3' | ZC3745 |
| SEQ. ID. No. 9 | 5'-GGCGAATTCGGAGCAGCTGCAGGGCTTCTG-3' | ZC3746 |
| SEQ. ID. No. 10 | 5'-AGGGAGACCGGAATTCGACTCGAGTCGACATCGATCAG-3' | ZC2633 |
| SEQ. ID. No. 11 | 5'-GACTCGAGTCGACATCGATCAGCCCCCCCCCC-3' | ZC2488 |

Double-stranded plasmids containing the 5' end of the GAD sequence inserted into pUC19 were sequenced in the same manner as the positive clones initially isolated from the library using the primers in Table 3.

TABLE 3

| | |
|---|---|
| SEQ. ID. No. 12 | 5'-GGCGATTAAGTTGGGTAA-3' |
| SEQ. ID. No. 13 | 5'-TAACAATTTCACACAGG-3' |

The entire sequence of the human islet cell GAD cDNA is shown in FIGS. 2a–2e, SEQ. ID. NO. 1. It was determined by assembling a composite of two overlapping cDNA clones, PHIG 11 and pHIG1.9, and of five RACE reaction products, RACE 20, 28A, 47A, 41 and 42 (FIG. 1). The two cDNA clones overlap by 110 bp and the five RACE sequences were designed to overlap with PHIG 1.9 by 140 nucleotides at the 3' end (FIG. 1). The pHIG 1.9 clone comprises 1900 bp and encodes the pyridoxal 5'-phosphate binding site (Pro-His-Lys-Met-Met-Gly) at amino acids 394–399, (included within SEQ ID NO:2) a stop codon following the C-terminal Leu codon and a polyadenylation site (AAATAAA), (bases 2329–2335 of SEQ ID NO:1), 17 nucleotides upstream of a poly A sequence at the 3' end

EXAMPLE II

Tissue Expression and Chromosomal Location of Human Islet GAD

Northern blot analysis was used to detect human islet GAD mRNA expression in normal human islets as well as in different in vitro cultured beta-cell lines. Beta-cell lines from rat (RIN-5AH-B), mouse (NIT cells) and hamster (HIT) cells of low passage number were cultured at 37° C. in 150 cm$^2$ tissue culture flasks in RPMI 1640 medium supplemented with 10% (v/v) heat-inactivated fetal calf serum, 20 mmol/l Hepes, 2 mmol/l L-glutamine, 24 mmol/l NaHCO$_3$, 100 U/ml penicillin and 100 μg/ml streptomycin (RPMI medium). The results were obtained with cells plated in a standardized manner at a density of 23×10$^3$ cells per cm$^2$. After 3 days to allow establishment of the culture, the medium was renewed. At this timepoint, referred to as day 0, the cell density was approximately 1×10$^5$ cells per cm$^2$. Over the next 4 days (days 1–4) the cells were collected for analysis of GAD gene expression by Northern blotting. The cells were detached after washing in Ca$^{2+}$- and Mg$^{2+}$-free Earle's medium by incubation at 37° C. for 5 min. in Earle's medium supplemented with 0.25% (w/v) trypsin (GIBCO BRL, Gaithersburg, Md.) and 1 mmol/l EDTA. After detachment, the cells were washed and immediately lysed for mRNA isolation as described in Example I above.

Northern blot analysis was performed as follows. About 5 pg poly A⁺RNA, estimated at $A_{260}$, was heated to 95° C. for 2 min. and separated by 1% agarose formaldehyde gel electrophoresis. Following separation, the agarose gel was washed twice for 20 min. in 10×saline-sodium-citrate buffer (SSC), the RNA blotted overnight onto a nitrocellulose filter (Scheicher & Schuell, Inc., Keene, N.H.) and the filter baked for 2 h at 80° C. as described (Davis, et al., *Basic Methods Molec. Biol* Elsevier, Amsterdam, 1986). The cDNA or oligonucleotide probes as described above were used after nick translation (GIBCO BRL) according to instructions provided by the manufacturer. Following 4 h prehybridization at 42° C., fresh hybridization buffer containing the single-stranded probe at about $10^6$ CPM/ml was added to the filter and hybridized overnight at 42° C. as described (Davis, et al., ibid). The filter was washed 3× for 20 min. at room temperature in 2×SSC containing 0.1% SDS and 2× for 20 min. in 2×SSC containing 0.1% SDS at 42° C. before it was exposed to X-ray film (X-omat XAR, Eastman Kodak, Rochester, N.Y.). Before reprobing, the filter was washed 3×5 min. in 0.2×SSC, 0.1% SDS at 95° C.

Northern blot analysis revealed a pronounced 5.7 kb transcript in poly A⁺RNA isolated from islets of dog and rat, as well as from brain of dog, monkey and rat. Expression of the human islet GAD was not detected in RIN-5AH cells, AL-34 cells, rat liver, muscle, testis and kidney. Reprobing the Northern blots with a probe representing the rat brain GAD cDNA revealed a 3.7 kb transcript not only in dog and rat brain, but also in the RIN cells. No cross hybridization to the 5.6 kb transcript was detected.

Genomic DNA from cells of patients with IDDM and from healthy individuals were probed in Southern blots with human islet GAD cDNA. The genomic DNA (20 μg) was digested with different restriction enzymes followed by electrophoretic separation on agarose gels. The pattern obtained with the human islet GAD cDNA probe was clearly different from that obtained with rat brain GAD cDNA probe, suggesting that the fragment patterns were generated by different genes.

EXAMPLE III

Detection of GAD Autoantibodies

The GAD cDNA was inserted into the vector pcDNAII (Invitrogen, San Diego, Calif.) to construct pEx9 and transcribed in vitro. A reaction mixture was prepared by combining 20 μl of 5×SP6 transcription buffer (GIBCO BRL); 10 μl of 100 mM DTT; 100 units RNAsin; 7.5 μl of 2.5 mM each ATP, CTP and UTP; 2.5 μl of 1 mM GTP; 5 μl of 5 mM m7GpppG (cap analog); 2 μg linearized pEx9 DNA; 2 μl SP6 polymerase (GIECO BRL) and distilled water to a final volume of 100 μl. The reaction mixture was incubated for 90 minutes at 37° C. The mixture was phenol-chloroform-isoamylalcohol extracted and then ethanol precipitated. The RNA pellet was resuspended in distilled water to a final concentration of 1 mg/ml.

The resulting synthetic mRNA was subjected to in vitro translation with $^{35}$S-methionine in a rabbit reticulocyte lysate system. The in vitro translation (IVT) reaction mixture contained 35 μl nuclease-treated rabbit reticulocyte lysate (Promega, Madison, Wis.), 50 units RNAsin, 1 μl amino acid mix (-Met), 1 μl $^{35}$S-methionine at a concentration of 150 Ci/mmol and 50 mCi/ml, and distilled water to a volume of 48 μl. The SP6 RNA, prepared as described above, was denatured at 67° C. for 10 minutes and then placed on ice. One microgram of the denatured SP6 RNA in a final volume of 2 μl was added to the IVT reaction mixture. The reaction mixture was incubated at 30°0 C. for 90 minutes. Two microliters of the reaction was precipitated with TCA to calculate percent incorporation as described by Sambrook et al. (ibid). The in vitro synthesized product represented a single Mr 64,000 protein.

The labeled, synthesized protein was used to screen sera for the presence of GAD autoantibodies. Protein A-Sepharose immunoprecipitation showed that sera from ten newly diagnosed IDDM children precipitated 11.6±2.9% (mean ±SEM) of the total radioactivity, compared with 2.3±0.5% in 22 healthy controls (p<0.001). Gel electrophoresis and autoradiography revealed that healthy controls remained negative while 8/10 IDDM sera precipitated the in vitro-synthesized protein. The specific immunoprecipitation with IDDM sera indicates that the major autoepitope is likely present on the nascent polypeptide and does not require post-translational modifications by an intact cell.

In a similar experiment, in vitro-synthesized, $^{35}$S-methionine-labeled GAD was used in an overnight radioligand binding assay using protein A-Sepharose to separate bound from free ligand. IMP buffer was prepared using 150 mM NaCl, 20 mM Tris pH 7.4, 1% Triton X-100, 0.1% Aprotinin, and 10 mM Benzamidine. A high salt IMP buffer was prepared with 400 mM NaCl substituted for the 150 mM NaCl. Forty-seven and one-half microliters of IMP buffer was added to 0.5 μl in vitro translated GAD and 2 μl of sera. The mixture was incubated by rotating overnight at 4° C. The Protein A-Sepharose was prewashed with IMP buffer and aliquoted into tubes at 50 μl/tube. The tubes were rotated for 1 hour at 4° C. The Protein A-Sepharose was then washed three times with 400 μl IMP buffer, one time with 400 μl high salt IMP buffer and one time with 400 μl IMP buffer. One hundred microliters of 1×SDS sample buffer, without any dyes, was added to each tube, and the mixture was boiled for 10 minutes. The supernatants were removed, added to 4 ml of scintillation fluid and counted. GAD antibody-positive (the Juvenile Diabetes Foundation serum for ICA standardization) and negative control sera were included in each assay to express autoantibody levels as a 64K index. A 64K index is defined as:

$$\frac{\text{mean cpm (sample)} - \text{mean cpm (negative control)}}{\text{mean cpm (positive control)} - \text{mean cpm (negative control)}}$$

The intra-assay coefficient of variation for duplicate determinations was 10.5%. In 38 0–15 year old controls the 64 K index was −0.031±0.007 (mean ±SEM). In 62 new onset, 0–15 year old IDDM patients, the 64K index was 0.48±0.082. At a dilution of 1:25, the IDDM sera precipitated 11.7±1.6% of the total ligand radioactivity compared to 1.9±0.1% in the controls (p<0.001). Using a 64K index of 0.03 as the upper level of normal, no control (0/38) was positive compared to 48/62 (77%) of the IDDM patients. The 64K index in IDDM correlated to levels of ICA ($r_s$= 0.58; p<0.001). Thus, autoantibodies against synthetic human islet GAD can be accurately detected in a radioligand assay and are closely associated with newly diagnosed IDDM in children.

EXAMPLE IV

Expression of GAD cDNA

Expression of the human islet GAD cDNA required that the two overlapping clones, pHIG11 and pHIG1.9 (Seq. ID.

No. 1) be assembled into a single full length clone. The 5' sequence from the open reading frame of clone pHIG11 was isolated using a polymerase chain reaction. Oligonucleotides were synthesized so the 5' end of one primer was positioned at the ATG initiation codon and contained the following sequence:

5' CCA GTC TGA ATT CAC CAT GCT AGC CCA GGC TCC GGA T 3' (Seq. ID. No. 14)

The 3' oligonucleotide primer began at a NsiI sits, 482 nucleotides downstream of the initiation codon, and contained the following sequence:

5' TTT TAG AGA AGC TTG GCA ATG CAT CAA AAT TTC CTC C 3' (Seq. ID. No. 15).

A 0.5 kb DNA fragment was isolated by digestion at the EcoRI (5') and HindIII (3') restriction sites, and after sequence analysis was found to be the correct size. The EcoRI site was altered to a BamHI site using the synthetic oligonucleotide 5' ATT GGA TCC 3'. The resulting 0.5 kb DNA fragment was then isolated using the BamHI (5') and the NaiI (3') restriction sites.

The remaining DNA sequence of the GAD cDNA was isolated as 2 cDNA fragments from the clone designated pHIG1.9 (Seq. ID. No. 1). The internal DNA fragment was isolated using the restriction enzymes NsiI (5') and BglII (3'). The resulting fragment was found to be 0.6 kb. The 3' end of the GAD cDNA sequence was isolated by digestion of the clone pHIG1.9 with the restriction enzymes BglII (5') and XbaI (3'), and the resulting fragment was found to be 0.72 kb.

The expression plasmid was made from a four-part ligation reaction that included the 5' BamHI-NsiI fragment, the internal NsiI-BglII fragment, the 3' BglII-XbaI fragment and the expression vector Zem 219b.

The vector Zem 219b was constructed in the following manner. Plasmid pIC19R (Marsh et al., *Gene* 32:481–486 (1984)) was digested with SmaI and Hind III. The ori region of SV40 from map position 270 (PvuII) to position 5171 (HindIII) was then ligated to the linearized pIC19R to produce plasmid Zem67. This plasmid was then cleaved with Bgl II, and the terminator region from the human growth hormone gene (De Noto et al., *Nuc. Acids Res.* 9: 3719–3730 (1980)) was inserted as a Bgl II-BamH I fragment to produce plasmid Zem86. A synthesized human plasminogen activator (t-PA) pre-pro sequence in pUC8 was isolated by digestion with BamHI and XhoII. This fragment was inserted into Bgl II digested Zem86 to produce plasmid Zem88. Plasmid pDR1296 (ATCC 53347) was digested with Bgl II and BamH I, and the t-PA cDNA fragment was isolated and inserted into Bgl II-cut Zem88. The resultant plasmid was designated Zem94. The vector Zem99, comprising the MT-1 promoter, complete t-PA coding sequence, and the human growth hormone (hGH) terminator, was then assembled. A KpnI-BamHI fragment comprising the MT-1 promoter was isolated from MThGHll1 (Palmiter et al., *Science* 222:809–814 (1983)) and inserted into pUC18 to construct Zem93. Plasmid EV142, comprising MT-1 and hGH sequences in the pBR322 derivative pBX322 (Palmiter et al., ibid.), was digested with Eco RI, and the fragment comprising the MT-1 promoter and hGH terminator sequences was isolated. This fragment was cloned into Eco RI-digested pUC13 to construct plasmid Zem4. Zem93 was then linearized by digestion with Bgl II and Sal I, and the hGH terminator was purified. The t-PA pre-pro sequence was removed from the pUC8 vector as a Sau 3A fragment. The three DNA fragments were then joined to produce plasmid Zem97. Zem97 was cut with Bgl II and the Bgl II-BamH I t-PA fragment from pDR1296 was inserted. The resultant vector was designated Zem99. Plasmid pSV2-DHFR (Subramani et al., ibid.) was digested with Cfo I, and the fragment containing the DHFR cDNA and the 3' attached SV40 sequences was isolated, repaired, and ligated to BamHI linkers. After digestion with BamH I, an approximately 800 bp fragment containing the entire cDNA and the SV40 terminator region was purified and ligated to BamHI-digested pUC8. Zem67 was digested with Bgl II and ligated with the BamHI DHFR-SV40 fragment to generate plasmid Zem176. Plasmid Zem93 was digested with Sst I and re-ligated to generate plasmid Zem106, in which approximately 600 bp of sequence 5' to the MT-1 promoter was eliminated. Plasmid Zem106 was digested with Eco RI and ligated to the EcoRI fragment containing the DHFR gene from plasmid Zem176. The resulting plasmid was designated Zts13. Plasmid Zts13 was digested with BamHI and ligated to the BamHI fragment from plasmid Zem99 containing the entire t-PA coding region and hGH terminator sequence. The resulting plasmid was designated Zts15. Zts15 was partially digested with BamHI, repaired and re-ligated to generate plasmid Zem219, in which the 3' BamHI site was destroyed. Plasmid Zem219 was partially digested with XbaI, repaired and re-ligated to generate plasmid Zem219a, in which the XbaI site 3' to the hGH terminator was destroyed. Zem219b was derived from Zem219a by digesting that vector with BamHI and XbaI, removing the t-PA sequences, and ligating the vector fragment with a BamHI-XbaI adaptor. Zem219b has been deposited with American Type Culture Collection, Rockville, Md. as an *E. coli* XL1-blue transformant.

Expression of the GAD cDNA was achieved by transfection of the tk⁻ts13 BHK cell line (ATCC CRL 1632) using the calcium phosphate method (Van der Eb, ibid.). Transfectants were selected using a medium containing 400 nM methotrexate. The transfectants were tested for production of human GAD protein using immunocytochemistry. For testing immunoreactivity, two antibodies were used (Michelsen et al., *Proc, Natl. Acad. Sci. USA* 88:8754–8758 (1991)). The first antibody, designated 1266, was raised in rabbits immunized with the synthetic C-terminal sequence:

Thr-Gln-Ser-Asp-Ile-Asp-Phe-Leu-Ile-Glu-Glu-Ile-Glu-Arg-Leu-Gly-Gln-Asp-Leu (Seq. ID. No. 16)

The second antibody used for immunofluorescence labeling was raised against GABA (Immunotech, Marseille, France). The two-color double immunofluorescence labeling was carried out on fixed (1% paraformaldehyde, neutral) monolayers of transfected BHK cells to test the co-localization of the immunoreactivities of the C-terminal antiserum 1266 and antiserum against GABA. Texas Red-goat anti-rabbit IgG (1:100 dilution; Axell (Westbury, N.Y.)) was used to detect primary antibodies. These assays showed that BHK cells transfected with human GAD cDNA expressed immunoreactive material while host cells without the GAD cDNA did not demonstrate reactivity.

The recombinant GAD protein was purified from confluent cultures of $9.5 \times 10^8$ transfected cells. The cells were pelleted by centrifugation at 350×g at room temperature for 4 minutes. The resulting cell pellet was homogenized in 20 ml of 50 mM sodium phosphate, 1 mM pyridoxal 5'-phosphate (PLP), 1 mM amino-ethyl-isothiouronium-bromide (AET), 1 mM EDTA, 0.05% W/V aprotinin, 1% W/V Triton X-114 (TX-114) pH 8.0 (buffer A) and shaken gently for 1 hour at 4' C. for 30 minutes. once in suspension the mixture was centrifugated at 100,000∴g at 4° C. for 30 minutes. Twenty milliters of supernant was poured on top of 20 ml of 6% (w/v) sucrose, and the mixture was heated to 30° C. for 3 minutes. Following incubation the mixture was centrifuged at 3290×g for 5 minutes. The aqueous phase was extracted as described previously by adding 0.5% w/v TX-114 and applied to the same sucrose fraction as used previously. Nine ml of buffer A without TX-114 was added to the 1 ml detergent phase. The diluted TX-114 detergent phase of 10 ml was applied to a 1.0×1.6 cm GAD-1-Sepharose affinity column. GAD-1 is a monoclonal antibody against the human GAD protein. The column was washed in 40 ml of buffer A. The sample was applied to the column a total of three times. After the final application the column was washed with 70 ml of 50 mM sodium phosphate, 1 mM PLP, 1 mM AET, 0.05% aprotinin and 1% w/v n-octyl glucoside pH 8.0 (buffer B). The GAD was eluted with 50 mM $NH_4HCO_3$, 1% w/v n-octyl glucoside, 1 mM PLP and 1 mM AET pH 9.5 and collected in 500 µl fractions. Five hundred microliters of 50 mM sodium phosphate pH 7.0 was added to each fraction. The column was washed in buffer B and stored in PBS and 0.02% $NaN_3$. Ten microliter aliquots of the first ten fractions were analyzed using 1D-SDS polyacrylamide gel electrophoresis. Using a polyclonal antibody raised against the C-terminus of the human GAD protein, western analysis was done. In addition, the gel was stained with Coomassie brilliant blue, and enzymatic activity was measured as described in Wu (*Methods in Enzymology* 113:3–10 (1985)). Pools 4–14 were combined, and the total protein yield was calculated to be 27 µg or 27 ng/$10^6$ BHK cells. The protein purity was evaluated using a 2D-PAGE analysis, which showed a major band at 64 kD.

The foregoing provides isolated and purified human islet cell GAD nucleotide sequences and recombinant human islet GAD polypeptides. These results offer, inter alia, a reproducible system to detect autoantibodies to the Mr 64,000 autoantigen in sera from patients with insulin-dependent diabetes or individuals with subclinical disease. oligonucleotide probes for detecting the islet cell sequences in itu are also provided by means of the present invention, as well as therapeutic approaches to preventing or alleviating diseases related to an autoimmune response to the human islet GAD antigen.

Although the foregoing invention has been described in some detail by way of illustration and example for purposes of clarity of understanding, it will be apparent that certain changes and modifications may be practiced within the scope of the appended claims.

What is claimed is:

1. An isolated polypeptide which is encoded by a DNA construct for the expression of a human pancreatic islet glutamic acid decarboxylase polypeptide fragment, which comprises the following operably linked elements:
   a transcriptional promoter;
   a peptide encoding DNA sequence consisting of a sequence that encodes said polypeptide fragment, wherein the polypeptide fragment is selected from residues 137–171, 165–195, 394–399, 405–431, 511–540, 567–585 of SEQ ID NO:2; and
   a transcriptional terminator.

2. The polypeptide of claim 1, wherein the DNA sequence that encodes said polypeptide fragment is from the corresponding sequence of the nucleotide sequence of SEQ ID NO:1.

3. An isolated human pancreatic islet glutamic acid decarboxylase polypeptide fragment consisting of residues 137–171, 165–195, 394–399, 405–431, 511–540, or 567–585 of SEQ ID NO:2.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 2370 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 38..1792

(xi) SEQUENCE DESCRIPTION: SEQ ID NO:1:

```
GGCACTCGCT GGCGACCTGC TCCAGTCTCC AAAGCCG ATG GCA TCT CCG GGC TCT        55
                                        Met Ala Ser Pro Gly Ser
                                         1               5

GGC TTT TGG TCT TTC GGG TCG GAA GAT GGC TCT GGG GAT TCC GAG AAT       103
Gly Phe Trp Ser Phe Gly Ser Glu Asp Gly Ser Gly Asp Ser Glu Asn
             10                  15                  20

CCC GGC ACA GCG CGA GCC TGG TGC CAA GTG GCT CAG AAG TTC ACG GGC       151
Pro Gly Thr Ala Arg Ala Trp Cys Gln Val Ala Gln Lys Phe Thr Gly
         25                  30                  35

GGC ATC GGA AAC AAA CTG TGC GCC CTG CTC TAC GGA GAC GCC GAG AAG       199
Gly Ile Gly Asn Lys Leu Cys Ala Leu Leu Tyr Gly Asp Ala Glu Lys
     40                  45                  50

CCG GCG GAG AGC GGC GGG AGC CAA CCC CCG CGG GCC GCC GCC CGG AAG       247
Pro Ala Glu Ser Gly Gly Ser Gln Pro Pro Arg Ala Ala Ala Arg Lys
 55                  60                  65                  70

GCC GCC TGC GCC TGC GAC CAG AAG CCC TGC AGC TGC TCC AAA GTG GAT       295
Ala Ala Cys Ala Cys Asp Gln Lys Pro Cys Ser Cys Ser Lys Val Asp
                 75                  80                  85

GTC AAC TAC GCG TTT CTC CAT GCA ACA GAC CTG CTG CCG GCG TGT GAT       343
Val Asn Tyr Ala Phe Leu His Ala Thr Asp Leu Leu Pro Ala Cys Asp
```

-continued

```
                   90                    95                     100
GGA GAA AGG CCC ACT TTG GCG TTT CTG CAA GAT GTT ATG AAC ATT TTA        391
Gly Glu Arg Pro Thr Leu Ala Phe Leu Gln Asp Val Met Asn Ile Leu
            105                     110                 115

CTT CAG TAT GTG GTG AAA AGT TTC GAT AGA TCA ACC AAA GTG ATT GAT        439
Leu Gln Tyr Val Val Lys Ser Phe Asp Arg Ser Thr Lys Val Ile Asp
    120                     125                 130

TTC CAT TAT CCT AAT GAG CTT CTC CAA GAA TAT AAT TGG GAA TTG GCA        487
Phe His Tyr Pro Asn Glu Leu Leu Gln Glu Tyr Asn Trp Glu Leu Ala
135                 140                     145                 150

GAC CAA CCA CAA AAT TTG GAG GAA ATT TTG ATG CAT TGC CAA ACA ACT        535
Asp Gln Pro Gln Asn Leu Glu Glu Ile Leu Met His Cys Gln Thr Thr
                    155                     160                 165

CTA AAA TAT GCA ATT AAA ACA GGG CAT CCT AGA TAC TTC AAT CAA CTT        583
Leu Lys Tyr Ala Ile Lys Thr Gly His Pro Arg Tyr Phe Asn Gln Leu
            170                     175                 180

TCT ACT GGT TTG GAT ATG GTT GGA TTA GCA GCA GAC TGG CTG ACA TCA        631
Ser Thr Gly Leu Asp Met Val Gly Leu Ala Ala Asp Trp Leu Thr Ser
        185                     190                 195

ACA GCA AAT ACT AAC ATG TTC ACC TAT GAA ATT GCT CCA GTA TTT GTG        679
Thr Ala Asn Thr Asn Met Phe Thr Tyr Glu Ile Ala Pro Val Phe Val
    200                     205                 210

CTT TTG GAA TAT GTC ACA CTA AAG AAA ATG AGA GAA ATC ATT GGC TGG        727
Leu Leu Glu Tyr Val Thr Leu Lys Lys Met Arg Glu Ile Ile Gly Trp
215                     220                 225                 230

CCA GGG GGC TCT GGC GAT GGG ATA TTT TCT CCC GGT GGC GCC ATA TCT        775
Pro Gly Gly Ser Gly Asp Gly Ile Phe Ser Pro Gly Gly Ala Ile Ser
                235                     240                 245

AAC ATG TAT GCC ATG ATG ATC GCA CGC TTT AAG ATG TTC CCA GAA GTC        823
Asn Met Tyr Ala Met Met Ile Ala Arg Phe Lys Met Phe Pro Glu Val
            250                     255                 260

AAG GAG AAA GGA ATG GCT GCT CTT CCC AGG CTC ATT GCC TTC ACG TCT        871
Lys Glu Lys Gly Met Ala Ala Leu Pro Arg Leu Ile Ala Phe Thr Ser
        265                     270                 275

GAA CAT AGT CAT TTT TCT CTC AAG AAG GGA GCT GCA GCC TTA GGG ATT        919
Glu His Ser His Phe Ser Leu Lys Lys Gly Ala Ala Ala Leu Gly Ile
    280                     285                 290

GGA ACA GAC AGC GTG ATT CTG ATT AAA TGT GAT GAG AGA GGG AAA ATG        967
Gly Thr Asp Ser Val Ile Leu Ile Lys Cys Asp Glu Arg Gly Lys Met
295                     300                 305                 310

ATT CCA TCT GAT CTT GAA AGA AGG ATT CTT GAA GCC AAA CAG AAA GGG       1015
Ile Pro Ser Asp Leu Glu Arg Arg Ile Leu Glu Ala Lys Gln Lys Gly
                315                     320                 325

TTT GTT CCT TTC CTC GTG AGT GCC ACA GCT GGA ACC ACC GTG TAC GGA       1063
Phe Val Pro Phe Leu Val Ser Ala Thr Ala Gly Thr Thr Val Tyr Gly
            330                     335                 340

GCA TTT GAC CCC CTC TTA GCT GTC GCT GAC ATT TGC AAA AAG TAT AAG       1111
Ala Phe Asp Pro Leu Leu Ala Val Ala Asp Ile Cys Lys Lys Tyr Lys
        345                     350                 355

ATC TGG ATG CAT GTG GAT GCA GCT TGG GGT GGG GGA TTA CTG ATG TCC       1159
Ile Trp Met His Val Asp Ala Ala Trp Gly Gly Gly Leu Leu Met Ser
    360                     365                 370

CGA AAA CAC AAG TGG AAA CTG AGT GGC GTG GAG AGG GCC AAC TCT GTG       1207
Arg Lys His Lys Trp Lys Leu Ser Gly Val Glu Arg Ala Asn Ser Val
375                     380                 385                 390

ACG TGG AAT CCA CAC AAG ATG ATG GGA GTC CCT TTG CAG TGC TCT GCT       1255
Thr Trp Asn Pro His Lys Met Met Gly Val Pro Leu Gln Cys Ser Ala
                395                     400                 405

CTC CTG GTT AGA GAA GAG GGA TTG ATG CAG AAT TGC AAC CAA ATG CAT       1303
```

```
Leu Leu Val Arg Glu Glu Gly Leu Met Gln Asn Cys Asn Gln Met His
        410                 415                 420

GCC TCC TAC CTC TTT CAG CAA GAT AAA CAT TAT GAC CTG TCC TAT GAC    1351
Ala Ser Tyr Leu Phe Gln Gln Asp Lys His Tyr Asp Leu Ser Tyr Asp
            425                 430                 435

ACT GGA GAC AAG GCC TTA CAG TGC GGA CGC CAC GTT GAT GTT TTT AAA    1399
Thr Gly Asp Lys Ala Leu Gln Cys Gly Arg His Val Asp Val Phe Lys
        440                 445                 450

CTA TGG CTG ATG TGG AGG GCA AAG GGG ACT ACC GGG TTT GAA GCG CAT    1447
Leu Trp Leu Met Trp Arg Ala Lys Gly Thr Thr Gly Phe Glu Ala His
455                 460                 465                 470

GTT GAT AAA TGT TTG GAG TTG GCA GAG TAT TTA TAC AAC ATC ATA AAA    1495
Val Asp Lys Cys Leu Glu Leu Ala Glu Tyr Leu Tyr Asn Ile Ile Lys
            475                 480                 485

AAC CGA GAA GGA TAT GAG ATG GTG TTT GAT GGG AAG CCT CAG CAC ACA    1543
Asn Arg Glu Gly Tyr Glu Met Val Phe Asp Gly Lys Pro Gln His Thr
        490                 495                 500

AAT GTC TGC TTC TGG TAC ATT CCT CCA AGC TTG CGT ACT CTG GAA GAC    1591
Asn Val Cys Phe Trp Tyr Ile Pro Pro Ser Leu Arg Thr Leu Glu Asp
            505                 510                 515

AAT GAA GAG AGA ATG AGT CGC CTC TCG AAG GTG GCT CCA GTG ATT AAA    1639
Asn Glu Glu Arg Met Ser Arg Leu Ser Lys Val Ala Pro Val Ile Lys
        520                 525                 530

GCC AGA ATG ATG GAG TAT GGA ACC ACA ATG GTC AGC TAC CAA CCC TTG    1687
Ala Arg Met Met Glu Tyr Gly Thr Thr Met Val Ser Tyr Gln Pro Leu
535                 540                 545                 550

GGA GAC AAG GTC AAT TTC TTC CGC ATG GTC ATC TCA AAC CCA GCG GCA    1735
Gly Asp Lys Val Asn Phe Phe Arg Met Val Ile Ser Asn Pro Ala Ala
            555                 560                 565

ACT CAC CAA GAC ATT GAC TTC CTG ATT GAA GAA ATA GAA CGC CTT GGA    1783
Thr His Gln Asp Ile Asp Phe Leu Ile Glu Glu Ile Glu Arg Leu Gly
        570                 575                 580

CAA GAT TTA TAATAACCTT GCTCACCAAG CTGTTCCACT TCTCTAGAGA            1832
Gln Asp Leu
        585

ACATGCCCTC AGCTAAGCCC CCTACTGAGA AACTTCCTTT GAGAATTGTG CGACTTCACA  1892

AAATGCAAGG TGAACACCAC TTTGTCTCTG AGAACAGACG TTACCAATTA TGGAGTGTCA  1952

CCAGCTGCCA AAATCGTAGG TGTTGGCTCT GCTGGTCACT GGAGTAGTTG CTACTCTTCA  2012

GAATATGGAC AAAGAAGGCA CAGGTGTAAA TATAGTAGCA GGATGAGGAA CCTCAAACTG  2072

GGTATCATTT GCACGTGCTC TTCTGTTCTC AAATGCTAAA TGCAAACACT GTGTATTTAT  2132

TAGTTAGGTG TGCCAAACTA CCGTTCCCAA ATTGGTGTTT CTGAATGACA TCAACATTCC  2192

CCCAACATTA CTCCATTACT AAAGACAGAA AAAAATAAAA ACATAAAATA TACAAACATG  2252

TGGCAACCTG TTCTTCCTAC CAAATATAAA CTTGTGTATG ATCCAAGTAT TTTATCTGTG  2312

TTGTCTCTCT AAACCCAAAT AAATGTGTAA ATGTGGACAC AAAAAAAAAA AAAAAAA    2370

(2) INFORMATION FOR SEQ ID NO:2:

(i) SEQUENCE CHARACTERISTICS:
        (A) LENGTH: 585 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ser Pro Gly Ser Gly Phe Trp Ser Phe Gly Ser Glu Asp Gly
1               5                   10                  15
```

-continued

```
Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
            50                  55                  60

Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
            85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125

Ser Thr Lys Val Ile Asp Phe His Tyr Pro Asn Glu Leu Leu Gln Glu
            130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
            165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
            210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
            245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
            325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
            370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Gly Leu Met Gln
            405                 410                 415

Asn Cys Asn Gln Met His Ala Ser Tyr Leu Phe Gln Gln Asp Lys His
            420                 425                 430
```

```
Tyr Asp Leu Ser Tyr Asp Thr Gly Asp Lys Ala Leu Gln Cys Gly Arg
        435                 440                 445
His Val Asp Val Phe Lys Leu Trp Leu Met Trp Arg Ala Lys Gly Thr
    450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Tyr Ile Pro Pro Ser
            500                 505                 510
Leu Arg Thr Leu Glu Asp Asn Glu Glu Arg Met Ser Arg Leu Ser Lys
        515                 520                 525
Val Ala Pro Val Ile Lys Ala Arg Met Met Glu Tyr Gly Thr Thr Met
    530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
        580                 585
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3338

(xi) SEQUENCE DESCRIPTION: SEQ ID NO:3:

GCGGGAGCGG ATCCTAATAC TACCAACCTG CG                           32

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3339

(xi) SEQUENCE DESCRIPTION: SEQ ID NO:4:

ACCATGGTTG TTCCTGACTC CATCAT                                   26

(2) INFORMATION FOR SEQ ID NO:5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3337

(xi) SEQUENCE DESCRIPTION: SEQ ID NO:5:

CTGACATCAA CTGCCAATAC CAATATGTTC ACATATGAAA TTGCA 45

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3614

(xi) SEQUENCE DESCRIPTION: SEQ ID NO:6:

AAATGAGAAT TCACACGCCG GCAGCAGGTC 30

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3623

(xi) SEQUENCE DESCRIPTION: SEQ ID NO:7:

AAGGAATTCA AGTTGATTGA AGTATCT 27

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3745

(xi) SEQUENCE DESCRIPTION: SEQ ID NO:8:

GGCGAATTCG CATATTTTAG AGTTGTTTGG 30

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (vii) IMMEDIATE SOURCE:
        (B) CLONE: ZC3746

(xi) SEQUENCE DESCRIPTION: SEQ ID NO:9:

GGCGAATTCG GAGCAGCTGC AGGGCTTCTG 30

(2) INFORMATION FOR SEQ ID NO:10:

```
    (i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: other nucleic acid (vii) IMMEDIATE SOURCE:
         (B) CLONE: ZC2633

(xi) SEQUENCE DESCRIPTION: SEQ ID NO:10:

AGGGAGACCG GAATTCGACT CGAGTCGACA TCGATCAG                              38

(2) INFORMATION FOR SEQ ID NO:11:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:11:

GACTCGAGTC GACATCGATC AGCCCCCCCC CC                                    32

(2) INFORMATION FOR SEQ ID NO:12:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:12:

GGCGATTAAG TTGGGTAA                                                    18

(2) INFORMATION FOR SEQ ID NO:13:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:13:

TAACAATTTC ACACAGG                                                     17

(2) INFORMATION FOR SEQ ID NO:14:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: other nucleic acid (xi) SEQUENCE DESCRIPTION: SEQ ID NO:14:

CCAGTCTGAA TTCACCATGC TAGCCCAGGC TCCGGAT                               37

(2) INFORMATION FOR SEQ ID NO:15:
```

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: other nucleic acid (xi) SEQUENCE DESCRIPTION: SEQ ID NO:15:

TTTTAGAGAA GCTTGGCAAT GCATCAAAAT TTCCTCC                                37

(2) INFORMATION FOR SEQ ID NO:16:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: other nucleic acid (xi) SEQUENCE DESCRIPTION: SEQ ID NO:16:

Thr Gln Ser Asp Ile Asp Phe Leu Ile Glu Glu Ile Glu Arg Leu Gly
1               5                   10                  15
Gln Asp Leu